(12) United States Patent
Moffett

(10) Patent No.: US 10,441,807 B2
(45) Date of Patent: Oct. 15, 2019

(54) TREATMENT OF CONDITIONS SUSCEPTIBLE TO PULSED ELECTROMAGNETIC FIELD THERAPY

(71) Applicant: REGENESIS BIOMEDICAL, INC., Scottsdale, AZ (US)

(72) Inventor: John Moffett, Phoenix, AZ (US)

(73) Assignee: Regenesis Biomedical, Inc., Scottsdale, AZ (US)

( * ) Notice: Subject to any disclaimer, the term of this patent is extended or adjusted under 35 U.S.C. 154(b) by 24 days.

(21) Appl. No.: 15/527,977

(22) PCT Filed: Nov. 23, 2015

(86) PCT No.: PCT/US2015/062232
§ 371 (c)(1),
(2) Date: May 18, 2017

(87) PCT Pub. No.: WO2016/081952
PCT Pub. Date: May 26, 2016

(65) Prior Publication Data
US 2017/0354830 A1 Dec. 14, 2017

Related U.S. Application Data

(60) Provisional application No. 62/082,825, filed on Nov. 21, 2014.

(51) Int. Cl.
*A61N 2/00* (2006.01)
(52) U.S. Cl.
CPC .............. *A61N 2/008* (2013.01); *A61N 2/004* (2013.01); *A61N 2/006* (2013.01)
(58) Field of Classification Search
CPC ......... A61N 2/004; A61N 2/006; A61N 2/008
USPC ....................................................... 600/9–15
See application file for complete search history.

(56) References Cited

U.S. PATENT DOCUMENTS

| | | | |
|---|---|---|---|
| 6,174,276 B1 | 1/2001 | Blackwell | |
| 6,334,069 B1 | 12/2001 | George et al. | |
| 6,443,883 B1 | 9/2002 | Ostrow et al. | |
| 6,463,336 B1 | 10/2002 | Mawhinney | |
| 8,195,287 B2* | 6/2012 | Dacey, Jr. | A61N 1/0556 607/2 |
| 2005/0059153 A1* | 3/2005 | George | A61N 1/00 435/446 |
| 2007/0060981 A1 | 3/2007 | Pilla et al. | |
| 2011/0196365 A1 | 8/2011 | Kim et al. | |
| 2012/0302821 A1 | 11/2012 | Burnett | |
| 2014/0012108 A1 | 1/2014 | McPeak | |
| 2014/0148870 A1* | 5/2014 | Burnett | A61N 1/0492 607/39 |
| 2014/0249355 A1 | 9/2014 | Martinez | |
| 2015/0297910 A1 | 10/2015 | Dimino et al. | |
| 2018/0043174 A1 | 2/2018 | Gurfein | |

FOREIGN PATENT DOCUMENTS

| | | |
|---|---|---|
| WO | WO2012/048302 A2 | 4/2012 |
| WO | WO2019/023265 A1 | 1/2019 |

OTHER PUBLICATIONS

Moffett et al, Activation of endogenous opioid gene expression in human keratin and fibroblasts by pulsed radiofrequency energy fields; Sep. 19, 2012; Journal of Pain Resereach; vol. 5, pp. 347-357.*
Apfelbaum et al.; Postoperative pain experience: results from a national survey suggest postoperative pain continues to be undermanaged; Anesthesia and Analgesia; 97(2); pp. 534-540; Aug. 2003.
Baranano et al.; Biliverdin reductase: a major physiologic cytoprotectant; Proceedings of the National Academy of Sciences; 99(25); pp. 16093-16098; Dec. 10, 2002.
Basbaum et al.; Cellular and molecular mechanisms of pain; Cell; 139(2); pp. 267-284; Oct. 16, 2009.
Catala; Five decades with polyunsaturated Fatty acids: chemical synthesis, enzymatic formation, lipid peroxidation and its biological effects; Journal of Lipids; http://dx.doi.org/10.1155/2013/710290; 20 pages; (year of pub. sufficiently earlier than effective US filing date and any foreign priority date) 2013.
Clark et al.; Neuropathic pain and cytokines: current perspectives; Journal of Pain Research; 6; pp. 803-814; doi: 10.2147/JPR. S53660; 12 pages; Nov. 21, 2013.
Commins et al.; The extended IL-10 superfamily: IL-10, IL-19, IL-20, IL-22, IL-24, IL-26, IL-28, and IL-29; Journal of Allergy and Clinical Immunology; 121(5); pp. 1108-1111; May 2008.
Dutra et al.; Heme on innate immunity and inflammation; Frontiers in Pharmacology; 5; Article 115; doi: 10.3389/fphar.2014.00115; 20 pages; May 2014.
Greene et al.; Regulation of inflammation in cancer by eicosanoids; Prostaglandins and Other Lipid Mediators; 96(1-4); pp. 27-36; 26 pages; (Author Manuscript); Nov. 2011.
Guo et al.; Pulsed radio frequency energy (PRFE) use in human medical applications; Electromagnetic Biology and Medicine; 30(1); pp. 21-45; Mar. 2011.
Hasegawa et al.; Modifying TNF alpha for therapeutic use: a perpective on the TNF receptor system; Mini Reviews in Medicinal Chemistry; 1(1); pp. 5-16; May 2001.

(Continued)

*Primary Examiner* — John P Lacyk
(74) *Attorney, Agent, or Firm* — Shay Glenn LLP

(57) ABSTRACT

The present disclosure relates to methods for treating diseases or conditions with pulsed electromagnetic field therapy, where the disease or condition treated is one susceptible to modulation of gene expression by pulsed electromagnetic field therapy. The present disclosure generally relates to methods of modulating gene expression and biological regulatory pathways with pulsed electromagnetic field therapy for treating diseases or conditions associated with such gene expression or regulatory pathways that are susceptible to modulation by pulsed electromagnetic therapy, including diseases or conditions associated with inflammation, nerve pain and wound repair.

19 Claims, 13 Drawing Sheets

(56) References Cited

OTHER PUBLICATIONS

Haworth et al.; Resolving the problem of persistence in the switch from acute to chronic inflammation; Proceedings of the National Academy of Sciences; 104(52); pp. 20647-20648; Dec. 26, 2007.
He et al.; Exposure to extremely low-frequency electromagnetic fields modulates Na+ currents in rat cerebellar granule cells through increase of AA/PGE2 and EP receptor-mediated cAMP/PKA pathway; Plos One; 8(1); pp. e54376; 13 pages; Jan. 22, 2013.
Heden et al.; Effects of pulsed electromagnetic fields on postoperative pain: a double-blind randomized pilot study in breast augmentation patients; Aesthetic Plastic Surgery; 32(4); pp. 660-666; Jul. 2008.
Ji et al; Emerging roles of resolvins in the resolution of inflammation and pain; Trenads in Neurosciences; 34(11); pp. 599-609; 20 pages; (Author Manuscript); Nov. 2011.
Kunkel et al.; Suppression of acute and chronic inflammation by orally administered prostaglandins; Arthritis and Rheumatism: Official Journal of the American College of Eheumatology; 24(9); pp. 1151-1158; Sep. 1981.
Livak et al.; Analysis of relative gene expression data using realtime quantitative PCR and the 2-??CT method; Methods; 25(4); pp. 402-408; Dec. 2001.
Medzhitov: Origin and physiological roles of inflammation; Nature; 454 (7203); pp. 428-435; Jul. 23, 2008.
Medzhitov; Inflammation 2010: new adventures of an old flame; Cell; 140(6); pp. 771-776; Mar. 19, 2010.
Moffett et al.; Activation of endogenous opioid gene expression in human keratinocytes and fibroblasts by pulsed radiofrequency energy fields; Journal of Pain Research; 5; pp. 347-357; (year of pub. sufficiently earlier than effective US filing date and any foreign priority date) 2012.
Moffett et al.; Pulsed radio frequency energy field treatment of cells in culture results in increased expression of genes involved in angiogenesis and tissue remodeling during wound healing; The Journal of Diabetic Foot Complications; 3(2); pp. 30-39; (year of pub. sufficiently earlier than effective US filing date and any foreign priority date) 2011.
Moffett et al.; Pulsed radio frequency energy field treatment of cells in culture results in increased expression of genes involved in inflammation phase of lower extremity diabetic wound healing; The Journal of Diabetic Foot Complications; 2(3); pp. 57-64; (year of pub. sufficiently earlier than effective US filing date and any foreign priority date) 2010.
Xu et al.; Resolvins RvE1 and RvD1 attenuate inflammatory pain via central and peripheral actions; Nature Medicine; 16(5); pp. 591-597; 10 pages; (Author Manuscript); May 2010.
Yang et al.; Metabolomics-lipidomics of eicosanoids and docosanoids generated by phagocytes; Current Protocols in Immunology; 95(1); pp. 14-26; 36 pages; (Author Manuscript); Nov. 2011.
Mosser et al.; Interleukin-10: new perspectives on an old cytokine; Immunological Reviews; 226(1); pp. 205-218; 22 pages; (Author Manuscript); Dec. 2008.
Nathan; Nonresolving inflammation; Cell; 140(6); pp. 871-882; Mar. 19, 2010.
Neher et al.; Molecular mechanisms of inflammation and tissue injury after major trauma is complement the "bad guy"?; Journal of Biomedical Sciences; 18(1); pp. 90; doi: 10.1186/1423/1423-0127-18-90; Dec. 2011.
Novo et al.; Redox mechanisms in hepatic chronic wound healing and fibrogenesis; Fibrogenesis and tissue repair; 1(1); doi:10.1186/1755-1536-1-5; 58 pages; Dec. 2008.
Pelletier et al.; New tricks from an old dog: mitochondria) redox signaling in cellular inflammation; InSeminars in Immunology; 24(6); pp. 384-392; 21 pages; (Author Manuscript); Dec. 2012.
Rohde et al.; Effects of pulsed electromagnetic fileds on interleukin-1 beta and postoperative pain: a double-blind, placebo-controlled, pilot study in breast reduction patients; Plastic and Reconstructive Surgery; 125(6); pp. 1620-1629; Jun. 2010.
Ross et al.; Effect of pulsed electromagnetic field on inflammatory pathway markers in RAW 264.7 murine macrophages; Journal of Inflammation Research; 6; pp. 45-51; (year of pub. sufficiently earlier than effective US filing date and any foreign priority date) 2013.
Serhan et al.; Anti-inflammatory and proresolving lipid mediators; Annu. Rev. Pathmechdis. Mech. Dis.; 3; pp. 279-312; 43 pages; (Author Manuscript); Feb. 28, 2008.
Serhan et al.; Maresins: novel macrophage mediators with potent anti-inflammatory and proresolving actions; Journal of Experimental Medicine; 206(1); pp. 15-23; Jan. 16, 2009.
Serhan et al.; Protectins and maresins: New pro-resolving families of mediators in acute inflammation and resolution bioactive metabolome; Biochimica et Bipphysics Acta (BBA)—Molecular and Cell Biology of Lipid; 1851(4); pp. 397-413; 40 pages; (Author Manuscript); Apr. 30, 2015.
Serhan; Novel lipid mediators and resolution mechanisms in acute inflammation: to resolve or not?; The American Journal of Pathology; 177(4); pp. 1576-1591; Oct. 2010.
Serhan; Novel pro-resolving lipid mediators are leads for resolution physiology; Nature; 510(7503); pp. 92-101; 24 pages; (Author Manuscript); Jun. 2014.
Spite et al.; Resovins, specialized proresolving lipid mediators, and their potential roles in metabolic diseases; Cell Metabolism; 19(1); pp. 21-36; Jan. 7, 2014.
Serhan et al.; Resolving inflammation: dual anti-inflammatory and pro resolution lipid mediators; Nature Reviews Immunology; 8(5); pp. 349-361; 31 pages; (Author Manuscript); May 2008.
Stein et al.; Peripheral mechanisms of pain and analgesia; Brain Research Reviews; 60(1); pp. 90-113; 38 pages; (Author Manuscript); Apr. 2009.
Suleyman et al.; Anti-inflammatory and side effects of cyclooxygenase inhibitors; Pharmacological Reports; 59(3); pp. 247-258; May 2007.
Uddin et al.; Resolvins: natural agonists for resolution of pulmonary inflammation; Progress in Lipid Research; 50(1); pp. 75-88; 30 pages; (Author Manuscript); Jan. 31, 2011.
Wagener et al.; Different faces of the heme-heme oxygenase system in inflammation; Pharmacological Reviews; 55(3); pp. 551-571; Sep. 2003.
Wagener et al.; The heme-heme oxygenase system: a molecular switch in wound healing; Blood; 102(2); pp. 521-528; Jul. 15, 2003.
Wegiel et al.; Go green: the anti-inflammatory effects of biliverdin reductase; Frontiers in Pharmacology; 3; Article 47; doi: 10.3389/fphar.2012.00047; 8 pages; Mar. 16, 2012.
Akan et al.; Extremely low-frequency electromagnetic fields affect the immune response of monocyte-derived macrophages to pathogens; Bioelectromagnetics; 31(8); pp. 603-612; Dec. 2010.
Brennan et al.; Cytokine expression in chronic inflammatory disease; British Medical Bulletin; 51(2); pp. 368-384; Apr. 1995.
Buckley et al.; The resolution of inflammation; Nature Reviews Immunology; 13(1); pp. 59-66; Jan. 2013.
Gou et al.; Meta-analysis of clinical efficacy of pulsed radio frequency energy treatment; Annals of Surgery; 255(3); pp. 457-467; Mar. 2012.
Markov et al.; Interaction between electromagnetic fields and the immune system: possible mechanisms for pain control; Ayrapetyan SNM, M.S., ed.; Bioelectromagnetics Current Concepts; Dordrecht: Springer; pp. 213-225; (year of pub. sufficiently earlier than effective US filing date and any foreign priority date) 2006.
McIntyre et al.; Molecular mechanisms of early inflammation; Thromb Haemost; 78(I):302-305; Jul. 1997.
Medzhitov et al.; Transcriptional control of the inflammatory response; Nature Reviews Immunology; 9(10); pp. 692-703; Oct. 2009.
Moreland; Inhibitors of tumor necrosis factor for rheumatoid arthritis; 66(6); pp. 367-374; Jun. 1999.
Moreland; Inhibitors of tumor necrosis factor for rheumatoid arthritis; The Journal of Rheumatology; 57; pp. 7-15; May 1, 1999.
Pilla et al.; EMF signals and ion/ligand binding kinetics: prediction of bioeffective waveform parameters; Bioelectrochemisrty and Bioenergetics; 48(1); pp. 27-34; Feb. 1999.
Pilla et al.; Nonthermal electromagnetic fields: from first messenger to therapeutic applications; Electromagnetic Biology and Medicine; 32(2); pp. 123-136; Jun. 2013.

(56) References Cited

OTHER PUBLICATIONS

Pons et al.; Pro-inflammatory and anti-inflammatory effects of the stable prostaglandin D2 analogue; European Journal of Pharmacology; 261(3); pp. 237-247; Aug. 22, 1994.
Ross et al.; Effect of time-varied magnetic field on inflammatory response in macrophage cell line RAW 264.7; Electromagnetic Biology and Medicine; 32(1); pp. 59-69; Mar. 2013.
Selvam et al.; Low frequency and low intensity pulsed electromagnetic field exerts its antinflammatory effect through restoration of plasma membrane calcium; Life Sciences; 80(26); pp. 2403-2410; Jun. 6, 2007.
Cho et al.; Discovery of (2-fluoro-benzyl)-(2-methyl-2 phenethyl-2H-chromen-6-yl)-amine (KRH-102140) as an orally active 5-lipoxygenase inhibitor with activity in murine inflammation models; Pharmacology; 87(1-2); pp. 49-55; Feb. 2011.
Vilcek; The cytokines: an overview; In: Thomson WAaMTL, ed.; The Cytokine Handbook. 4 ed. San Diego: Academic Press, Calif, USA; pp. 1-18; (year of pub. sufficiently earlier than effective US filing date and any foreign priority date) 2012.
Yang et al.; Reactive oxygen species in the immune system; International Reviews of Immunology; 32(3); pp. 249-270; Jun. 2013.
Yeretssian et al; Molecular regulation of inflammation and cell death; Cytokine; 43(3); pp. 380-390; Sep. 2008.

\* cited by examiner

TREATMENT OF CONDITIONS SUSCEPTIBLE TO PULSED ELECTROMAGNETIC FIELD THERAPY

CROSS REFERENCE TO RELATED APPLICATIONS

This application claims priority to U.S. Provisional Application No. 62/082,825, entitled "MODULATION OF THE INFLAMMATION PATHWAY USING PULSED ELECTROMAGNETIC FIELD THERAPY," which was filed on Nov. 21, 2014, and which is incorporated by reference herein in its entirety.

BACKGROUND

Field

The present disclosure relates to methods of modulating gene expression and biological regulatory pathways with pulsed electromagnetic field therapy for treating diseases or conditions associated with such gene expression or regulatory pathways that are susceptible to modulation by pulsed electromagnetic therapy, including diseases or conditions associated with inflammation, nerve pain and wound repair.

Discussion of the Background Art

Development of multicellular organisms relies on an orchestrated regulation of when and where gene expression occurs, as related to any of growth, stasis, and response to external stimuli, among others. For example, the formation of the intricate anatomical features of internal organs or the proper migration of nerves throughout the body require that each participating cell sense its environment and respond appropriately to developmental cues. The requirement for regulated proliferation is equally important for the proper functioning of the mature multicellular organism. The average adult human eradicates 50-70 billion cells in the body each day, and a commensurate number of replacement cells must be produced daily. The number and type of cells that are induced to proliferate as replacements depends upon the circumstances under which the original cells were eradicated and the tissues affected.

Harnessing the body's ability to regulate spatial and temporal aspects of inflammation and cell proliferation is one approach to treating various conditions and disease.

Inflammation is a complex process involving distinct but overlapping biochemical and molecular events that are highly regulated. The inflammation process involves an acute, pro-inflammatory phase followed by modulation of the acute inflammatory response and a subsequent return to homeostasis. Various inflammation-related physiological processes involved in a response to tissue trauma and associated mediators are illustrated in FIG. 1. As shown in FIG. 1, tissue trauma can produce pro-inflammatory heme. Heme is catabolized by heme oxygenase (HO), and the activity of HO is known to downregulate acute inflammation. Likewise, various antioxidant enzymes may contribute to dampening and resolution of an inflammatory response by removal of pro-inflammatory reactive oxygen species (ROS) that may be produced in an inflammation response to trauma. Lipid mediator metabolic pathways are involved in different stages of the inflammatory response to trauma, and contribute to the biosynthesis of lipid mediators involved in the acute inflammatory response (e.g. prostaglandins, leukotrienes) as well as inflammation resolution (lipoxins, resolvins, marisins, protectins). The interplay between cycloxygenase (COX) and lipoxygenase (LOX) pathways involved in lipid mediator class switching (from pro-inflammatory to resolution-mediating) is an important step in initiating the resolution of inflammation.

Normal regulation of the inflammatory response involves temporal and spatial regulation of gene expression in the various cell types involved. While the inflammatory response is protective in nature, dysregulation of the acute or resolution phases can lead to chronic inflammation and other disease conditions, including as further described herein.

Pain, including chronic pain is a multifaceted condition and may be associated with any of muscle pain, joint pain and nerve pain. Each has various distinct and overlapping modalities, and may be associated with dysregulation of the acute inflammatory response, or other factors. A patient's perceived pain sensitivity and pain threshold are common indicators of pain. The relative nerve fiber density of patient can often impact perceived pain, as well as new nerve fiber sprouting (axonal sprouting).

Wound repair likewise employs a complex most of gene expression and biological pathway regulation. Wound treatment and wound physiology in response to treatment likewise is believed to comprise a variety interacting physiological mechanisms. Each mechanism may comprise differential expression and activity of genes and gene products involved in wound repair processes, as well as other physiological processes. Such gene expression may be further differentiated according to cell type For example, there are three phases associated with the process of wound healing, including the inflammatory phase, the proliferative phase, and the remodeling phase. During the inflammatory phase, bacteria and debris are removed and macrophages release growth factors to stimulate angiogenesis and the production of fibroblasts. During the proliferative phase, granulation tissue forms and epithelialization begins, which involves migration of epithelial cells to seal the wound; fibroblasts proliferate and synthesize collagen to fill the wound and provide a strong matrix on which epithelial cells grow; and contractile cells called myofibroblasts appear in the wound and aid in wound closure. During the remodeling phase, collagen associated with scar formation undergoes repeated degradation and resynthesis, wherein the tensile strength of the newly formed skin increases. During acute inflammation, resident and recruited cells alike produce pro-inflammatory mediators including pro-inflammatory eicosanoids and pro-inflammatory cytokines. The COX and LOX enzymatic pathways, respectively, may produce pro-inflammatory eicosanoids and leukotrienes, but also are necessary for production of lipid mediators involved in programmed resolution, namely eicosanoid mediators of lipid mediator class switching (in the case of COX), and pro-resolving metabolites (in the case of LOX). Both of these pathways are targets for pharmaceutical drugs for the treatment of inflammation.

Pulsed electromagnetic field (PEMF) therapy is an emerging field with promise in treating a variety of conditions and disease. PEMF therapy is a device-based therapy used for non-invasive delivery of pulsed electromagnetic fields to various patient target tissues.

For example, the PROVANT® PEMF system by Regenesis Biomedical, Inc. (Scottsdale, Ariz.) is an exemplary system approved for use in treating pain and edema following surgery involving soft tissue. Based on this treatment success, various other indications benefiting from PEMP therapy have been proposed. However, the underlying molecular and cellular effects of PEMF therapy are poorly understood. A need exists for determining new treatment indications utilizing PEMF therapy, as informed by further understanding of the underlying genes, cells, tissue types, biological pathways, and clinical markers corresponding to clinical conditions susceptible to treatment using PEMF energetics.

SUMMARY

The present disclosure generally relates to methods of modulating gene expression and biological regulatory pathways with pulsed electromagnetic field therapy for treating diseases or conditions associated with such gene expression or regulatory pathways that are susceptible to modulation by pulsed electromagnetic therapy, including diseases or conditions associated with inflammation, nerve pain and wound repair.

In various aspects, PEMF treatment is administered to a patient to modulate one or more of pain, a pain condition, a pain threshold, pain tolerance, nerve function, nerve fiber density, skin perfusion pressure, angiogenesis, wound healing, wound closure, and wound volume. In various aspects, PEMF treatment of a patient produces a measurable clinical effect associated with one or more of pain, a pain condition, a pain threshold, pain tolerance, nerve function, nerve fiber density, skin perfusion pressure, angiogenesis, wound healing, wound closure, and wound volume. In various aspects, PEMF treatment modulates gene expression of one or more genes associated with an inflammatory response pathway. In various aspects, PEMF treatment modulates gene expression of one or more genes associated with heme oxygenase, pro-oxidant enzymes, anti-oxidant enzymes, lipid mediator biosynthesis enzymes, prostaglandin biosynthesis enzymes, lipoxygenases, and interleukins. In various aspects, the disease or condition treated is one susceptible to modulation of gene expression of one or more genes associated with heme oxygenase, pro-oxidant enzymes, anti-oxidant enzymes, lipid mediator biosynthesis enzymes, prostaglandin biosynthesis enzymes, lipoxygenases, and interleukins by PEMF.

BRIEF DESCRIPTION OF THE DRAWINGS

The accompanying drawings, which are incorporated herein and form a part of the specification, illustrate the present disclosure and, together with the description, further serve to explain the principles of the disclosure and to enable a person skilled in the pertinent art to make and use the disclosed embodiments.

DETAILED DESCRIPTION

Figure 1:
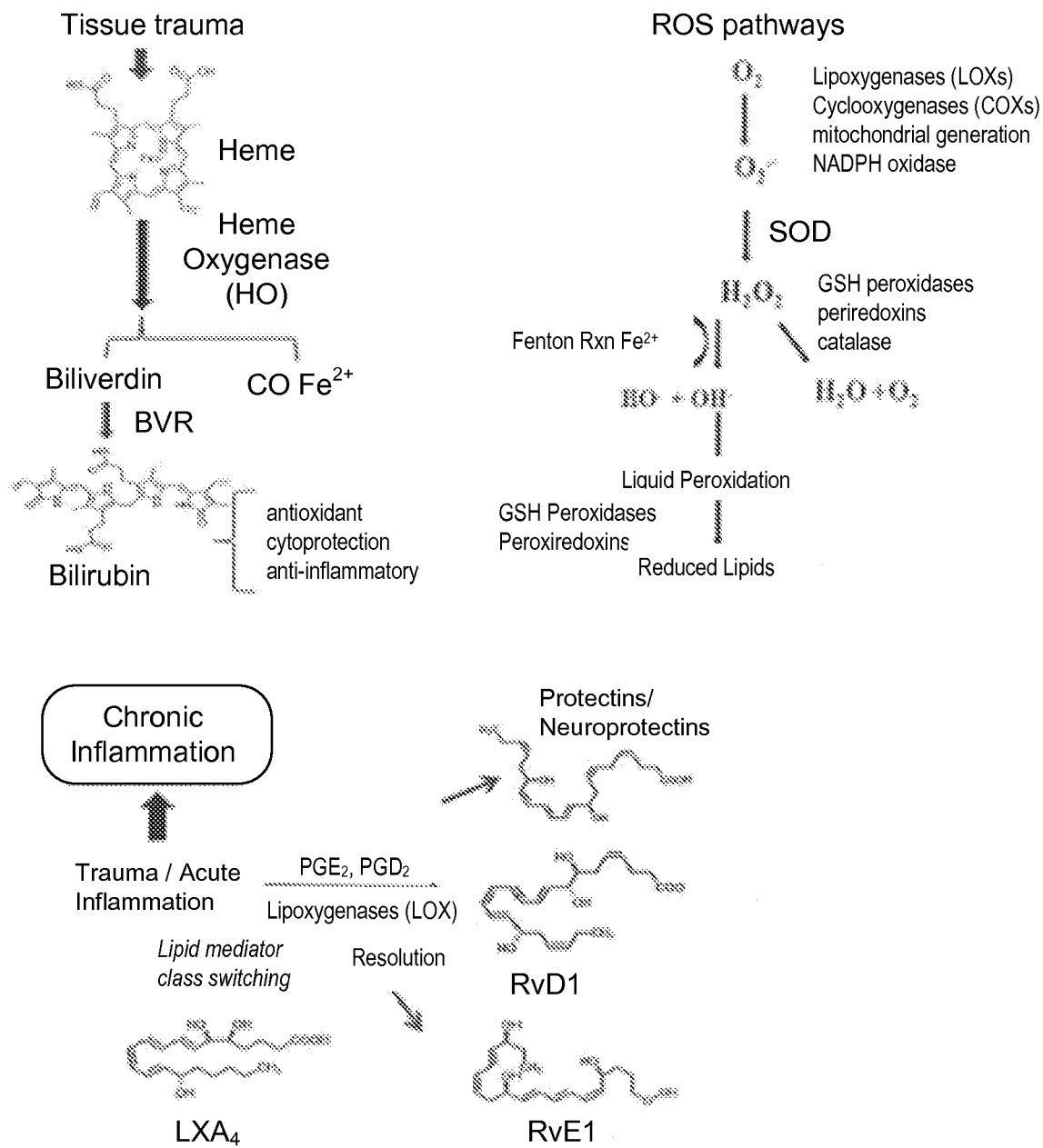
FIG. 1 illustrates various inflammation-related physiological processes.

The following detailed description is merely exemplary in nature and is not intended to limit the present invention, its applications, or its uses. The description of specific examples indicated in various aspects and embodiments are intended for purposes of illustration only and are not intended to limit the scope of the invention disclosed herein. Moreover, recitation of multiple aspects and embodiments having stated features is not intended to exclude other aspects and embodiments having additional features or incorporating different combinations of the features.

While the aspects and embodiments are described in sufficient detail to enable those skilled in the art to practice the invention, it should be understood that other aspects and embodiments may be realized and that logical changes may be made without departing from the spirit and scope of the invention. Thus, the detailed description herein is presented for purposes of illustration only and not of limitation. For example, steps or functions recited in descriptions, any method, system, or process, may be executed in any order and are not limited to the order presented. Furthermore, any reference to singular includes the plural, and any reference to the plural also includes the singular.

Definitions

Unless defined otherwise, all technical and scientific terms used herein have the same meaning as commonly understood by those of ordinary skill in the art to which this disclosure belongs. Although any methods and materials similar or equivalent to those described herein can be used in the practice of the subject matter herein, preferred methods and materials are described. For the purposes of the present disclosure, the following terms are defined below.

As used herein, the term "pulsed electromagnetic field" is intended to mean a nonionizing, non-thermal form of high intensity radiofrequency radiation with energy having both electric and magnetic components and properties of wavelength and frequency. The radiofrequency radiation used in the PEMF treatments described herein has a wavelength greater than about 1 meter.

As used herein, the term "modulate" includes to increase or decrease one or more quantifiable parameters, such as RNA or protein expression productions following gene expression modulation, optionally by a defined and/or statistically significant amount.

As used herein, a "target" includes an in vitro target or a clinical target. An "in vitro target" includes a cell culture, a tissue culture, an organ culture, and the like. A "clinical target" includes a treatment site of a subject or patient, including any identified anatomical region or location designated to receive PEMF treatment, including any tissue or organ associated with the site.

As used herein, "pain" associated diseases or conditions include pain sensitivity and pain threshold, including a patient's perceived pain sensitivity and pain threshold, as well the relative nerve fiber density in a patient and nerve fiber sprouting, also known as axonal sprouting.

As used herein, the term "axonal sprouting" means a process where fine nerve processes (sprouts) grow out from intact axons to reinnervate muscle fibers, optionally, wherein the sprouting helps to sustain the nerve supply to muscles and other tissues of the body.

As used herein, the term "tissue" is intended to mean a group of cells organized to perform a particular function. A group of cells included in the term can be organized in an ordered structure such as a tube or sheet. Alternatively a group of cells can be unstructured, for example, occurring in mass or clump. Examples of tissues include epithelial, connective, skeletal, muscular, glandular, and nervous tissues.

As used herein, the term "wound" is intended to mean a stress to a tissue due to injury. A stress to a tissue can involve a breach and included in the term can be a chronic wound, pressure ulcer, diabetic ulcer, venous stasis ulcer, burn or trauma. The term can include a stress or breach that is at a particular stage of healing including, for example, an inflammatory phase in which leukocytes migrate to the wound site and monocytes are converted to macrophages; proliferative phase in which granulation occurs due to proliferation of fibroblasts, production of a collagen matrix and vascularization; epithelialization phase in which epithelial cells grow along fibrin and myofibroblasts synthesize collagen; or differentiation phase in which collagen is degraded and resynthesized as the tissue is remodeled. A wound-associated disease or condition can include a variety of clinical indications associated with trauma, surgery and post-surgical conditions, chronic conditions, and the like. For example, wounds can include: chronic wounds; large, deep, open wounds; graft and flap site wounds; full thickness burns; partial thickness burns; diabetic ulcers; pressure ulcers; decubitus ulcers; arterial ulcers; avulsion injuries; pilonidal disease; cysts; acute wounds; tendon rupture wounds; postoperative incisions; postoperative wounds; traumatic wounds; dermatology conditions; scleroderma; atrophy blanche disease; trauma; bomb blast or other military-type inflicted wounds; gunshot wounds; bites; or wound dehiscence.

As used herein, a "PEMF system" is intended to mean a system used to generate and deliver a pulsed electromagnetic field.

As used herein, a PEMF system comprises an electromagnetic energy generator, a treatment applicator through which the PEMF is delivered from the PEMF signal generator to a treatment target, and a regulator for controlling the amount or characteristics of the electromagnetic energy delivered by the applicator. The regulator may be fixed or adjustable. An exemplary PEMF system for use in various methods herein is described in U.S. Pat. No. 6,334,069 B1, hereby incorporated by reference in its entirety, which describes an apparatus that includes a pulsed electromagnetic energy generator; a power controller, including a power level controller responsive to signals from multiple sensing and control circuits; and a treatment applicator. However, PEMF treatment can be administered to a treatment target using any apparatus capable of generating and applying electromagnetic energy of defined parameters to the treatment target.

In various aspects, PEMF treatment is delivered to treatment target with a PEMF system.

In accordance with various aspects and embodiments, parameters of a PEMF system, including electromagnetic energy parameters are selected. Exemplary parameters include, without limitation, pulse rate, pulse width, power level (i.e., electric field strength), duty cycle, and carrier frequency. The configuration of an antenna used for application of a PEMF treatment (also referred to herein as the "applicator"), described in more detail below, can also influence the effect of the PEMF treatment and further comprises a parameter of PEMF treatment.

The electric field strength is a quantitative expression of the intensity of an electric field at a particular location. In accordance with various embodiments, the electric field strength is selected from about 60 to about 1,065 V/m. Electric field strength (also referred to as the power level) produced by a PEMF system and a particular treatment applicator may be measured, estimated, or predicted based on the operating parameters of pulsed the electromagnetic field generator and the configuration of the treatment applicator. For example, in various embodiments, the predicted electric field strength of about 591 V/m at a distance of 5 cm from the surface of the treatment applicator. However, the electric field strength actually experienced at a treatment target site, such as a treatment target site comprising the tissue of a treated subject, may be difficult to measure. Accordingly, the power level used to describe a PEMF treatment may be a predicted or calculated electric field strength based on other controllable parameters of a particular PEMF generator and treatment applicator.

The duty cycle is the percentage of one period in which the electromagnetic field generator of the PEMF system is active. In accordance with various embodiments, the duty cycle of a PEMF system during application of PEMF treatment is selected from between about 0.4% and 10%, 0.6% and 9.5%, 0.8% and 9.0%, 1.0% and 8.5%, 1.5% and 8.0%, 2.0% and 7.5%, 2.5% and 7.0%, 3.0% and 6.5%, 3.5% and 6.0%, 4.0% and 5.5%, or 4.5% and 5.0%.

The carrier frequency of the PEMF system is generally a high intensity radiation frequency. In various embodiments, the carrier frequency may comprise a particular frequency approved for medical device use by the Federal Communications Commission (FCC). For example, a PEMF system may be selected, or PEMF treatment administered, with a carrier frequency of about 27.12 MHz. The pulse rate is the frequency at which electromagnetic pulses are transmitted. In various embodiments, a pulse rate of between about 1 Hz and about 4000 Hz is selected. In various embodiments, a pulse rate of about 1000 Hz is selected.

Pulse width is the duration of each electromagnetic pulse used in PEMF treatment. In various embodiments, a pulse width of between about 5 to about 300 microseconds per pulse is selected. In various embodiments, a PEMF system produces pulses with a pulse width of about 16 to about 195 microseconds per pulse. For example, in various embodiments, a pulse width of about 42 microseconds is selected.

In various aspects, one or more PEMF parameters is selected. In various embodiments, one or more PEMF parameters is selected for particular application of PEMF treatment to modulate desired gene expression and/or biological regulatory pathways, for treating an identified disease or condition. In further aspects and embodiments, the gene expression or regulatory pathway is susceptible to modulation by PEMF therapy. In further aspects and embodiments, the modulated gene expression produces a measurable clinical effect. The selected PEMF parameters may include those of the delivery of pulsed radiofrequency radiation energy with a predicted average electrical field strength of about 591 V/m, a pulse width of about 42 microseconds, and a pulse frequency of about 1,000 pulses per second, wherein these particular field strength, pulse width and pulse frequency settings pertain to the PROVANT device. Certain in vitro and clinical applications of PEMF treatments and therapy using these parameters are described below In accordance with various aspects and embodiments, these parameters can be selected for use in in vitro applications and in vivo treatment methods as described herein.

PEMF treatment may include an individual treatment or a series of treatments. A treatment target may include one or more cells in an in vitro cell or tissue culture. A treatment target can also comprise a treatment site of a clinical subject. PEMF treatment may be administered using an applicator included in a PEMF system. Various suitable applicators may be used. In various embodiments, the applicator comprises an applicator pad with an embedded flat spiral antenna having a radius of 7.5 cm made up of 6 turns at a width of 0.70 cm spaced with a separation of 0.3 cm. An exemplary applicator for use in various methods herein is described and illustrated in U.S. Pat. No. 6,334,069 B1. The PEMF is produced by an electromagnetic energy generator and delivered to a treatment target by the applicator. Such a configuration is capable of producing an electric field that extends from the surface of the pad and may be perceived or measured at some distance from the pad. In various embodiments, this distance is about 5 cm from the surface of the pad.

For in vitro treatment targets, a culture may be placed in a culture vessel at a fixed distance from the pad, such as a distance of about 5 cm, to provide a consistent electrical field strength between treatments. For clinical treatment targets, the treatment applicator may be placed in contact with or adjacent to the treatment site, such that the electric field projects into the tissue at the treatment site. As described above, the electrical field strength experience by the treated tissues of the patient at the treatment site due to penetration of the PEMF into the treated tissues is difficult to measure, and in various embodiments, the electrical field strength experienced by the treated tissue at a distance of about 5 cm from the surface of the applicator is a calculated electrical field strength. In various embodiments, the calculated electrical field strength at a distance of about 5 cm from the applicator is the same, regardless of whether the treatment target is an in vitro treatment target or a clinical treatment target.

The duration of PEMF delivery may be selected from any suitable treatment duration and frequency. PEMF treatment of a clinical target may include a single administration of PEMF therapy or multiple administrations. A single administration comprises application of a PEMF treatment for a dosage time. Multiple administrations can be provided over a period of, hours, days or weeks. For example, PEMF treatment may be administered with a dosage time of between about 1 minute and about 120 minutes, or between about 5 minutes and about 90 minutes, or between about 10 minutes and about 75 minutes, or between about 20 minutes and about 60 minutes, or between about 30 minutes and about 45 minutes per administration. Treatments comprising multiple administrations may be administered multiple times per day and/or over multiple days. For example, PEMF treatment may be administered twice daily, or three times daily, or four times daily, or any other suitable number. For treatments comprising twice daily administrations, individual administrations may be spaced to provide approximately 8-12 hours between administrations. For example, PEMF treatment may be administered as described in U.S. Pat. No. 6,334,069 B1. The treatment period can comprise a period of several days, such as about 7 days, or about 14 days, or about 30 days, or about 60 days, or about 90 days, according to the desired treatment indication.

PEMF treatment of an in vitro target may be delivered directly to a cell or to an environment of the cell such as a culture medium, tissue, fluid or organ in which the cell is located. For in vivo applications, PEMF treatment can be delivered directly to a target site to be treated or to a target site that is sufficiently proximal to that the intended target cell or tissue in order to receive the desired electromagnetic effect. For example, electromagnetic energy can be delivered externally to treat conditions or diseases that afflict cells of the skin or that afflict internally located cells that are electromagnetically affected by surface application of electromagnetic energy.

In various aspects, PEMF treatment is delivered to a target site to modulate the expression of an identified set of genes, and/or gene products. Such modulation may be associated with downstream modulation of cellular components including, without limitation, cell cycle regulators, signal transduction proteins, transcription factors, DNA synthesis proteins or receptors. For example, modulation of various genes associated with inflammatory regulatory pathways can affect treatment outcomes for patients suffering from certain inflammatory diseases or conditions. Modulation of various genes associated with pain receptor pathways can affect treatment outcomes for patients suffering from certain pain-associated diseases or conditions. Modulation of various genes associated with wound healing, for example certain angiogenesis factors, may affect treatment outcomes for patients suffering from wounds and wound-associated diseases or conditions.

Modulation of gene expression produced by application of PEMF treatment to in vitro or clinical targets can be assess by various methods suitable for evaluation of gene expression, such as quantitative real-time reverse transcription polymerase chain reaction assays. Various genes whose expression may by modulated by PEMF treatment according to the aspects and embodiments herein are further described in more detail in the Examples below. Moreover, in various embodiments, certain measurable clinical effects may be susceptible to modulation of gene expression and/or PEMF therapy in a cell, tissue, or organ in treatment site. Accordingly, in various embodiments, PEMF treatments can modulate gene expression and/or produce a clinical effect at a target site of a treated patient.

In various aspects, a PEMF treatment can produce modulation of gene expression of a single gene or a plurality of genes. This can produce modulation of the activity of the gene product or the gene function. In various embodiments, a gene product may be modulated by a PEMF treatment, notwithstanding a lack of modulation of expression of the same gene. In further embodiments, gene expression may be modulated by PEMF treatment without a corresponding modulation of the gene function. The level of expression or activity of a gene or gene product can be determined using methods well known in the art such as mRNA detection methods and protein detection methods. Additionally, activity of gene products can be measured using known enzyme assays such as kinase assays or binding assays that exploit interactions and activities such as those described above in regard to particular gene products.

In various aspects, modulation of expression of a plurality of genes can comprise upregulation of expression of each of the plurality of genes, downregulation of expression of each of the plurality of genes, or both upregulation and downregulation expression of various genes comprising the plurality of genes. For example, an increase or a decrease in expression comprises an increase or a decrease of at least 5%, 10%, 20%, 30%, 40%, 50%, 60%, 70%, 80%, 90%, 100%, 200%, 300%, 400% or 500%, and all values in between these stated percentages, relative to endogenous expression in the absence of PEMF treatment.

In various aspects, modulation of expression of a plurality of genes can comprise upregulation of expression of each of the plurality of genes, downregulation of expression of each of the plurality of genes, or both upregulation and downregulation expression of various genes comprising the plurality of genes.

In various aspects, a PEMF treatment can produce various patterns of differential modulation expression various genes in a plurality of genes. For example, a PEMF treatment may produce simultaneous upregulation of expression of a first gene and downregulation of expression of a second gene, as described above. Other patterns of differential modulation of gene expression are possible, such as upregulation of expression a first gene while producing no modulation of expression of a second gene. In various embodiments, a PEMF treatment can produce a pattern of differential modulation comprising a relative modulation, such as, relative modulation of two different upregulated genes. For example, in various embodiments, a PEMF treatment may produce a two-fold increase in the expression level of first gene and a four-fold increase in the expression level of a second gene, thereby producing a two-fold differential modulation of the second gene relative to the first gene.

In various aspects, modulation of gene expression and differential gene expression produced by a PEMF treatment may provide a sort of modulation "signature" may be specific to the PEMF system parameters and treatment indication. In various aspects and embodiments, a modulation signature "control" is defined by the relative gene expression levels in the absence of receiving PEMF treatment. PEMF treatment at a target site will modify this gene expression signature relative to the control. In accordance with further aspects and embodiments, one or more parameters of the PEMF system are selected to optimize gene expression, such as the modulation signature, for treatment of a disease or condition, for such diseases or conditions that are susceptible to treatment by such modulation. In further aspects and embodiments, diseases or conditions susceptible to treatment by such modulation are identified for treatment by PEMF therapy, where the device parameters are fixed or substantially fixed. A device having device parameters that are fixed or relatively fixed may include a device in which the device parameters may not be adjusted by the operator, or a device previously established parameters, where new indications for the existing parameters are identified.

In various embodiments, assessing modulation of a plurality of gene products may facilitate a determination of the effects that the treatment has upon a signal transduction pathway or a network of interacting pathways. Examples of methods known in the art for measuring the levels of a plurality of gene products include cDNA sequencing, clone hybridization, differential display, subtractive hybridization, cDNA fragment fingerprinting, serial analysis of gene expression (SAGE), and mRNA or protein microarrays. Methods of detecting the activity or level of one or more gene products can be performed either qualitatively or quantitatively.

PEMF treatment can be delivered to a target including a cell, tissue, or organ, in vitro or in vivo, using various methods described herein. Following treatment, the response of the cell or tissue to the PEMF treatment can be evaluated by obtaining a cell or tissue sample directly from the treatment site of the treated subject. A treated cell or tissue can be readily obtained from a subject using minimally invasive methods, for example, from fluids such as the blood or lymph or from accessible tissues such as the skin, hair follicles, cervix or cheek. Where necessary a cell can also be obtained using slightly more invasive procedures, such as a punch biopsy, needle biopsy, endoscope biopsy or surgical biopsy. Depending on the need and the availability of an appropriate procedure, cells from essentially any organ or tissue of the body can be obtained for use in a method of the invention. Those skilled in the art will know or be able to determine an appropriate method for obtaining a cell of interest based on various factors including, for example, the location of the cell and risk factors or preference of the individual from whom the cell is harvested.

In various aspects and embodiments, PEMF treatments are applied to cell culture lines.

In various and embodiments, PEMF treatments are applied patients at a treatment site.

In various aspects PEMF treatment is applied to a target site experiencing inflammation, for example, a treatment site comprising any of soft tissue or osseous tissue. Inflammation includes an inflammatory phase and a resolution phase. In various embodiments, PEMF treatment modulates gene expression of various genes involved in the acute and resolution phases of various cell types within a tissue.

In various embodiments, PEMF treatment modulates the expression of one or more genes encoding one or more enzymes relating to one or more of the following pathways: heme catabolism; removal of reactive oxygen species (ROS); and, mediation of lipid biosynthesis, such as occurring in selected cell and tissues types, including those associated with human dermal fibroblasts (HDF), human epidermal keratinocytes (HEK), and human mononuclear cells (HMNC). Likewise, PEMF treatment also modulates gene expression of several cytokine-related genes, in specified cell and tissue types, including those associated with HDF, HEK, and HMNC cell types.

Heme oxygenase (HO) is involved in catabolism of pro-oxidant heme. Following injury, free heme can serve as a pro-inflammatory signal, and thus its removal may be important for abating an unwanted inflammatory response. In various aspects, PEMF treatment modulates HO-1 gene expression in specified cell and tissue types, including those associated with HDF, HEK, and HMNC cells. In various aspects and embodiments, PEMF treatment increases expression of the HO-1 gene, or product associated with such gene, such as in a selected cell or tissue type. In further embodiments, at least one of PEMF treatment and an increase in HO-1 gene expression is associated with enhancing wound-healing treatment, and related diseases and conditions, such as in a selected cell or tissue type.

Reactive oxygen species (ROS) are chemically reactive molecules containing oxygen. Examples include peroxides, superoxide, hydroxyl radical, and singlet oxygen. In a biological context, ROS are formed as a natural byproduct of the normal metabolism of oxygen and have known roles in cell signaling and homeostasis. In various aspects and embodiments, PEMF treatment modulates genes associated with enzymes active in neutralizing oxygen radicals (also known as anti-oxidants) in specified cell and tissue types, including those associated with HDF, HEK, and HMNC cells. In various aspects and embodiments, PEMF treatment increases the expression of at least one of the following genes, CAT, GSR, PRDX-6, and SOD-3, or product associated with such genes, such as in a selected cell or tissue type. In further embodiments, at least one of PEMF treatment and increased expression of any of CAT, GSR, PRDX-6, and SOD-3 is associated with enhancing treatment of ROS-related diseases and conditions, such as in a selected cell or tissue type. Lipid mediators have important roles during both the acute and resolution phases of inflammation (FIG. 1). In accordance with various aspects and embodiments. A number of metabolites of omega-3 and -6 polyunsaturated fatty acids, such as prostaglandins, leukotrienes, lipoxins, resolvins, protectins, and maresins, function as bioactive Lipid mediators have important roles during both the acute and resolution phases of inflammation, and related diseases and conditions. In various aspects and embodiments, PEMF treatment modulates expression of prostaglandins, leukotrienes, lipoxins, resolvins, protectins, and maresins in specified cell and tissue types, including those associated with HDF, HEK, and HMNC cells. In various aspects and embodiments, PEMF treatment increases the expression of at least one of the following genes, COX-2, PTGDS, PTGES, PTGIS, or products associated with such genes, such as in a selected cell or tissue type. In various aspects and embodiments, PEMF treatment decreases the expression of at least one of the following genes, PTGDS, PTGES, PTGIS, or products associated with such genes, such as in a selected cell or tissue type. In further embodiments, at least one of PEMF treatment, increased expression of COX-2, PTGDS, PTGES, PTGIS, and decreased expression of PTGDS, PTGES, PTGIS, such as in a selected cell or tissue type, is associated with enhancing treatment of lipid-mediator related diseases and conditions.

In various aspects, PEMF treatment modulates lipoxygenase gene expression in specified cell and tissue types, including those associated with HDF, HEK, and HMNC cells. In various aspects and embodiments, PEMF treatment increases expression of the ALOX-12 gene, or product associated with such gene, such as in a selected cell or tissue type. In various aspects and embodiments, PEMF treatment decreases the expression of at least one of the ALOX-12 gene and ALOX-15 gene, or product associated with such genes, such as in a selected cell or tissue type. In further embodiments, at least one of PEMF treatment, an increase in the expression of ALOX-12, and a decrease in the expression of any of ALOX-12 and ALOX-15, in a selected cell or tissue type, is associated with enhancing treatment of lipoxygenases-related diseases and conditions.

In various aspects, PEMF treatment modulates interleukin gene expression in specified cell and tissue types, including those associated with HDF, HEK, and HMNC cells. In various aspects and embodiments, PEMF treatment increases expression of one of IL-2, IL-5, IL-6, IL-10, IL-12, IL-20 and IL-21 genes, or products associated with such genes, such as in a selected cell or tissue type. In various aspects and embodiments, PEMF treatment decreases the expression of at least one of IL-1α, IL-1β, IL-2, IL-5, IL-6, IL-10, IL-12, IL-20 and IL-21 genes, or products associated with such genes, such as in a selected cell or tissue type. In further embodiments, at least one of PEMF treatment, an increase in the expression of at least one of IL-1α, IL-1β, IL-2, IL-5, IL-6, IL-10, IL-12, IL-20 and IL-21 genes, and a decrease in the expression of IL-1α, IL-1β, IL-2, IL-5, IL-6, IL-10, IL-12, IL-20 and IL-21 genes, such as in a selected cell or tissue type, is associated with enhancing treatment of interleukin-related diseases and conditions.

In various embodiments, PEMF treatment modulates gene expression of HO, various cytokines, and/or genes involved in prostaglandin biosynthesis. Modulation of gene expression of these genes may produce one or more measurable clinical effects in a treated subject, including increased skin perfusion, increased nerve density, modulated nerve function, decreased pain score, increased pain tolerance, and increased pain threshold.

In various aspects and embodiments, PEMF treatment propagates the proliferative and remodeling phases associated with wound healing, including fibroblast and epithelial cell proliferation.

In various aspects and embodiments, PEMF treatment modulates or promotes wound healing and associated physiological processes, such as angiogenesis and/or skin perfusion associated with a treatment site, nerve density, nerve function, wound healing, and modulation of pain, including pain threshold, pain tolerance, and pain level. In various embodiments, PEMF treatment modulates gene expression of various genes associated with regulating and/or effecting an associated physiological processes responsible for producing the observed clinical effects. In further embodiments, PEMF treatment modulates various physiological processes susceptible to PEMF treatment, optionally including modulating a specified clinical effect.

In various aspects, PEMF treatment modulates nerve function. In various embodiments, PEMF treatment modulates nerve function associated with a treatment site. In various embodiments, PEMF treatment produces a measurable clinical effect associated with nerve function. Production of a measurable clinical effect may be evaluated using any suitable method, including, for example, one or more of as a sympathetic skin response test, a nerve conduction velocity test, a pain threshold test, and a pain tolerance test. In various embodiments, a PEMF treatment modulates expression of one or more genes associated with nerve function. In various embodiments, the one or more genes are selected from at least one pro-opioid gene, a cyclooxygenase (COX) gene, and an arachidonate lipoxygenase (ALOX) gene. In various embodiments, expression of a pro-opioid gene is increased relative to expression of a pro-opioid gene in the absence of PEMF treatment. An increase in expression comprises an increase of at least 5%, 10%, 20%, 30%, 40%, 50%, 60%, 70%, 80%, 90%, 100%, 200%, 300%, 400% or 500%, and all values in between these stated percentages, relative to endogenous expression in the absence of PEMF treatment. A pro-opioid gene includes at least one of a pro-opiomelanocortin (POMC) gene, a pro-enkephalin (PENK) gene, and a prodynorphin (PDYN) gene. In various embodiments, PEMF treatment modulates nerve function and expression of one or more of genes associated with nerve function. In various embodiments, PEMF treatment modulates nerve function, modulates expression of one or more of genes associated with nerve function, and produces a measurable clinical effect associated with nerve function. Without wishing to be bound by theory, modulation of pro-opioid genes may provide an analgesic mechanism in pain pathways responsive to tissue damage and injury.

In various aspects, PEMF treatment produces increased nerve fiber density in a tissue. In various embodiments, PEMF treatment produces increased nerve fiber density in a tissue associated with a treatment site. In various embodiments, PEMF treatment produces a measurable clinical effect associated with increased nerve fiber density in a tissue. Production of a measurable clinical effect associated with nerve fiber density can be evaluated using any suitable method, including, for example, a skin biopsy. In various embodiments, a PEMF treatment modulates expression of one or more genes associated with nerve fiber density, such as genes associated with nerve fiber sprouting or axonal sprouting. In various embodiments, the one or more genes associated with nerve fiber density include a nerve growth factor (NGF) gene. An increase in expression comprises an increase of at least 5%, 10%, 20%, 30%, 40%, 50%, 60%, 70%, 80%, 90%, 100%, 200%, 300%, 400% or 500%, and all values in between these stated percentages, relative to endogenous expression in the absence of PEMF treatment. In various embodiments, PEMF treatment modulates nerve fiber density and expression of one or more genes associated with nerve fiber density. In various embodiments, PEMF treatment modulates nerve fiber density, modulates expression of one or more genes associated with nerve fiber density, and produces a measurable clinical effect associated with nerve fiber density.

In various aspects, a PEMF treatment produces angiogenesis or increased skin perfusion in a tissue. In various embodiments, PEMF treatment produces angiogenesis or increased skin perfusion in a tissue associated with a treatment site. In various embodiments, PEMF treatment produces a measurable clinical effect associated with angiogenesis or skin perfusion in a tissue associated with a treatment site. Production of a measurable clinical effect associated with angiogenesis or skin perfusion can be evaluated using any suitable method, including, for example, one or more of microvascular scanning of the treated tissue and a skin perfusion pressure test. In various embodiments, a PEMF treatment modulates expression of one or more genes associated with angiogenesis or skin perfusion. In various embodiments, the one or more genes are selected from a vascular endothelial growth factor (VEGF) gene and a platelet-derived growth factor beta polypeptide (PDGFb) gene. An increase in expression comprises an increase of at least 5%, 10%, 20%, 30%, 40%, 50%, 60%, 70%, 80%, 90%, 100%, 200%, 300%, 400% or 500%, and all values in between these stated percentages, relative to endogenous expression in the absence of PEMF treatment. In various embodiments, PEMF treatment modulates angiogenesis or skin perfusion and expression of one or more genes associated with angiogenesis or skin perfusion. In various embodiments, PEMF treatment modulates angiogenesis or skin perfusion, modulates expression of one or more genes associated with angiogenesis or skin perfusion, and produces a measurable clinical effect associated with angiogenesis or skin perfusion.

Example 1

Effects of PEMF Treatment on Expression of Genes Related to Modulation of Inflammatory Response Pathways The effect of PEMF treatment on expression of genes involved in repressing or resolving inflammation was studied. PEMF treatments were applied to human dermal fibroblast (HDF) cells, human epidermal keratinocyte (HEK) cells, and human monocyte cells (HMNC) in culture. Enzymes involved in heme catabolism (heme oxygenase (HO)), lipid mediator biosynthesis (cyclooxygenases (COXs) and lipoxygenases (LOXs)), and reduction of reactive oxygen species (ROS) are illustrated in FIG. 1. Changes in gene expression for these enzymes in response to PEMF treatment, as well as changes in gene expression for cytokines believed to be involved in inflammation processes, were measured in the following experiments described in detail below.

Methods

Culture media for cell cultures was purchased from Cell Applications, Inc. (San Diego, Calif., USA) and Mediatech, Inc. (Herndon, Va., USA) for general culture of HDF, HEK, and HMNC cells. Fetal calf serum, penicillin/streptomycin, trypsin, 1× phosphate buffered saline, sodium pyruvate, and non-essential amino acids were purchased from HyClone Laboratories, Inc. (now GE Healthcare Life Sciences, Inc., Logan, Utah, USA). Reagents for RT-PCR were from Quanta BioSciences, Inc. (from VWR, Radnor, Pa., USA). Oligonucleotide primers for PCR were obtained from Real-TimePrimers, LLC (Elkins Park, Pa., USA). General chemicals were purchased from Sigma-Aldrich or VWR. Adult HDF, HEK and HMNC cells were purchased from Cell Applications, Inc. Routine cell culture was performed using methods described in Moffett et al., Pulsed Radio Frequency Energy Field Treatment of Cells in Culture Results in Increased Expression of Genes Involved in Angiogenesis and Tissue Remodeling During Wound Healing, J. Diabetic Foot Complications, 3(2):30-39 (2011); Moffett et al., Activation of Endogenous Opioid Gene Expression in Human Keratinocytes and Fibroblasts by Pulsed Radiofrequency Energy Fields, J. Pain Res. 5:347-357 (2011); and Moffett et al., Pulsed Radio Frequency Energy Field Treatment of Cells in Culture Results in Increased Expression of Genes Involved in the Inflammation Phase of Lower Extremity Diabetic Wound Healing. J. Diabetic Foot Complications, 2(3):57-64 (2010).

HDF, HEK, and HMNC cell production for PEMF treatments was performed using manufacturer recommendations for each cell type. All cells were grown in a in a humidified incubator at 37° C. and 5% $CO_2$. Cells were used for experimentation after 5-10 cell culture passages for HDF and HEK, or used 1 day after seeding for HMNC.

HDF cells (Cell Applications, Inc., catalog number 106k-05a) were cultured in 10 cm plates at a density of $1.14 \times 10^4$ cells/cm$^2$ in minimum essential media (MEM) supplemented with 1 mM sodium pyruvate, 1 mM non-essential amino acids, 100 units penicillin, 100 µg streptomycin, and 5% FCS.

HEK cells (Cell Applications, Inc., catalog number 102K-05a) were cultured in 10 cm plates at a density of $0.75 \times 10^4$ cells/cm$^2$ in keratinocyte growth media, supplied by the manufacturer. HEK cells were used for experimentation after 16 hours in a humidified incubator at 37° C. with 5% $CO_2$. HEK were used for experimentation from passage 3-7.

HMNC cells were cultured in 10 cm plates at a density of $5 \times 10^5$ cells/cm$^2$ in HMNC media (Cell Applications, Inc., catalog number 615-250) supplied by the manufacturer. Cells were suspended 16 hours prior to experimentation.

PEMF treatments were performed by exposing cells to the PEMF field produced by the PROVANT PEMF system. The PROVANT PEMF system is configured to produce a 27.12 MHz radio frequency (RF) signal transmitted from a flat spiral antenna with a radius of about 7.5 cm made up of about 6 turns at a width of about 0.70 cm spaced with a separation of about 0.3 cm. The signal was delivered in about 42 µsec pulses with a period of about 1 KHz. The calculated energy parameters for the field produced by the device using these setting are about 591 V/M and about 6.7 A/M in electrical and magnetic fields, respectively, at about 5 cm from the surface of the antenna. Cells were placed at a distance of about 5 cm from the antenna during treatment. Treatment was performed at room temperature for about 30 minutes and then cells were returned to the incubator.

Cells were harvested at four time points following PEMF treatment, including immediately following the 30 minute PEMF treatment, and at about 1 hour, 2 hours, and 4 hours after treatment initiation (i.e., 30 minutes, 1.5 hours, and 3.5 hours after completion of the 30 minute PEMF treatment). Total RNA was isolated from harvested cells for gene expression analysis, as described below.

RNA Isolation and Real-Time Quantitative Reverse Transcription Polymerase Chain Reaction (qRT-PCR)

Total RNA was isolated from harvested cells using an RNeasy Mini Kit (Qiagen Inc., Valencia, Calif., USA). Total RNA (0.05 µg) was reverse transcribed using qScript cDNA Synthesis Kits (Quanta BioSciences, Inc., purchased through VWR International, Cat. Number 101414-098) following the manufacturer's instructions.

Quantitative real-time PCR (qRT-PCR) was performed on a Rotor-Gene Q instrument (Qiagen) using 20 µl reaction volumes and the following thermal cycling program: an initial 10 minute 94° C. enzyme activation step, followed by 45 cycles of denaturation for 15 seconds at 94° C., annealing for 30 seconds at 55° C. and elongation for 30 seconds at 72° C. Primer oligonucleotide sequences are reported in Moffett et al., Activation of Endogenous Opioid Gene Expression in Human Keratinocytes and Fibroblasts by Pulsed Radiofrequency Energy Fields, J. Pain Res. 5:347-357 (2011) and Moffett et al., Pulsed Radio Frequency Energy Field Treatment of Cells in Culture Results in Increased Expression of Genes Involved in the Inflammation Phase of Lower Extremity Diabetic Wound Healing. J. Diabetic Foot Complications, 2(3):57-64 (2010). Quantitation and analysis of relative gene expression was performed using the $2^{-\Delta\Delta C_T}$ method as described by Livak and Schmittgen, Analysis of Relative Gene Expression Data Using Real-Time Quantitative PCR and the $2^{-\Delta\Delta C_T}$ Method, Methods 25(4): 402-40 (2001). Glyceraldehyde phosphate dehydrogenase (GAPDH) was used to normalize product expression between different RNA samples and treatments. RNA was isolated from at least 4 independent experiments and qRT-PCR was performed in triplicate. PCR products were electrophoresed on 2% agarose gels and stained with ethidium bromide to verify the fidelity of the PCR reaction. The relationship between the concentration of input RNA and the amount of PCR product was linear for each PCR product.

Statistical Analysis

RT-PCR data analyzed using one-way ANOVA. If the equal variance test failed for one-way ANOVA, the Dunn's method for multiple comparisons was used. For all the experiments reported a p-value of less than 0.05 was considered significant. All the data was analyzed using Sigma-Plot version 11.0 (Systat Software, Inc., San Jose, Calif., USA).

Results

PEMF treatment of HDF, HEK and HMNC cells produced changes in mRNA levels of a number of factors important for suppressing the acute inflammatory response and mediating active resolution of inflammation. These results are summarized in Table 1, below, and described in more detail in the following sections. The roles of the various genes in the inflammatory response are further illustrated in FIG. 6.

TABLE 1

Statistically-meaningful changes in transcript levels detected within 4 hours after PEMF treatment relative to untreated control cells.

|  | HDF | HEK | HMNC |
| --- | --- | --- | --- |
| Heme oxygenases (HO-1, HO-2) | HO-1* | HO-1* | HO-1** |
| Pro-oxidant enzymes | NOX* | — | NOX |
| Anti-oxidant enzymes | CAT | CAT | GSR |
|  | GSR | PRDX-6 | PRDX-6 |
|  | PRDX-6 | SOD-3 | SOD-3 |
|  | SOD-3 |  |  |
| Lipid mediator biosynthesis enzymes | | | |
| Prostaglandin synthesis enzymes | COX-2 PTGDS PTGES* PTGIS | PTGIS | PTGDS PTGES PTGIS |
| Lipoxygenases | ALOX-12 | ALOX-15 | ALOX-12 ALOX-15 |
| Interleukins | IL-1β* IL-6 IL-10* IL-12 | IL-1β IL-6 IL-10* IL-12* | IL-1β IL-5 IL-12 IL-20 IL-21 |

Notes:
p < 0.05 or better were met in all cases; p < 0.01 and greater denoted by asterisks (p < 0.01* and p < 0.001**).
Abbreviations: HO, heme oxygenase; NOX, NADPH-oxidase; CAT, catalase; COX, cyclooxygenase; GPX-3, glutathione peroxidase-3; GSR, glutathione reductase; PRDX-6, periredoxin-6; SOD-3, superoxide dismutase-3; PTGDS, prostaglandin D2 synthase; PTGES, prostaglandin E2 synthase; PTGIS, prostaglandin I2 synthase; ALOX, arachidonate lipoxygenase, IL, interleukin.

Figure 2A:
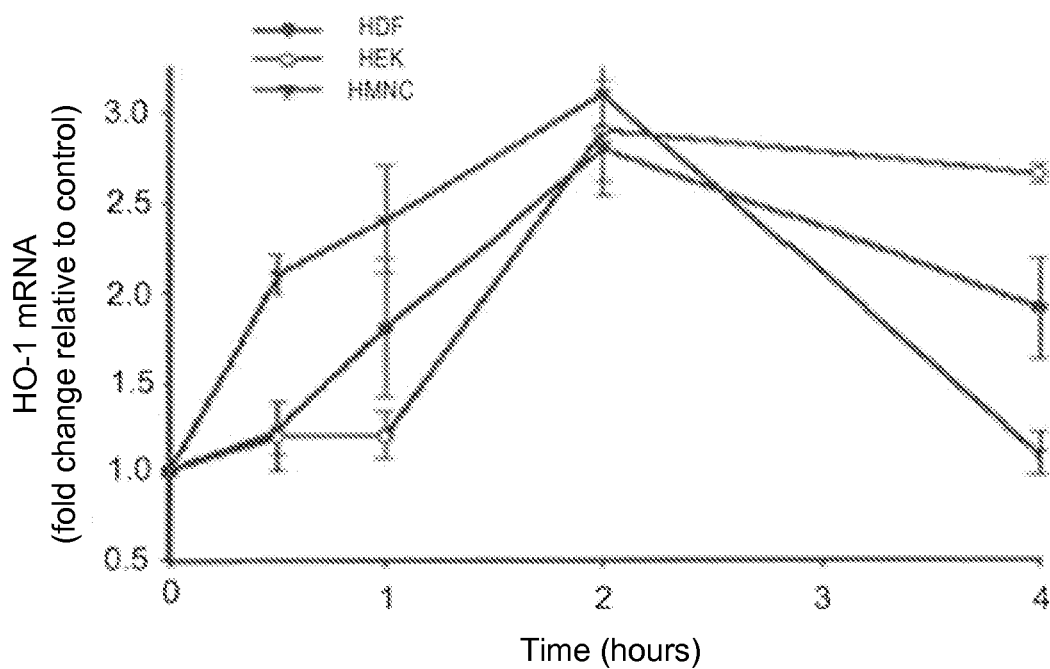
FIGS. 2A and 2B illustrate the effects of PEMF treatment on heme oxygenase expression in HEK, HDF and HMNC cells.
Figure 2B:
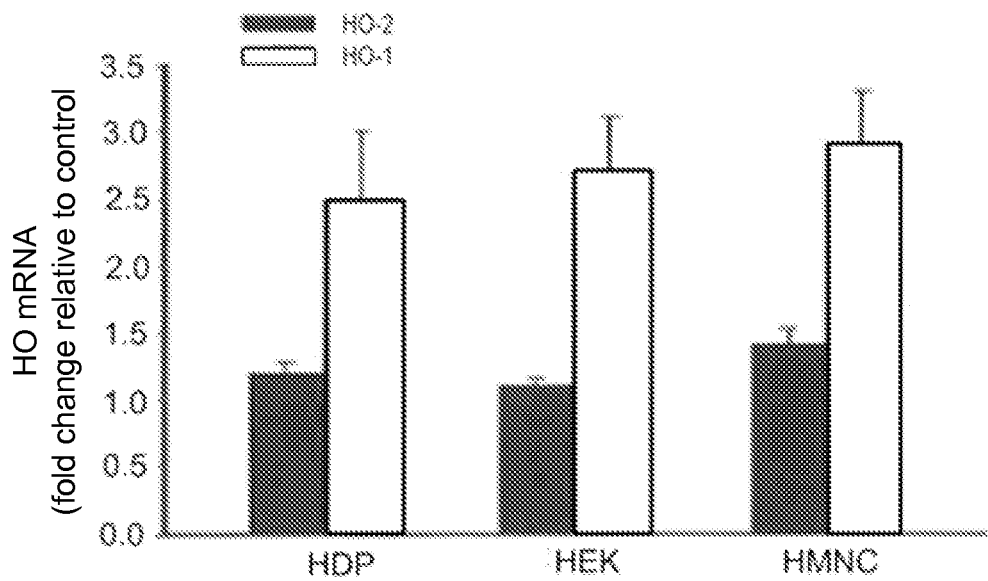

PEMF Treatment of HDF, HEK and HMNC Cells Produces an Increase in Heme Oxygenase Transcript Levels To evaluate whether PEMF might also affect HO-1 expression, cultured HDF, HEK, and HMNC were treated with PEMF for 30 minutes and measured changes in HO-1 mRNA levels were following treatment. Each of the HDF, HEK, and HMNC cell types showed a significant increase in HO-1 gene expression relative to untreated cells. HDF and HEK cells showed similar patterns of enhanced HO-1 gene expression after treatment with PEMF, while HMNC cells showed a more rapid increase (FIG. 2A). Maximum transcript levels were observed at about 2 hours after the initiation of PEMF of treatment for all three cell types. Unexpectedly, the increase in HO-1 gene expression relative to untreated cells ranged from 2.5- to 2.9-fold, depending on the cell type, at 2 hours after initiation of treatment using the PROVANT device in in vitro treatment conditions. In contrast, HO-2 expression was relatively unchanged in all three cell types at this time point (FIG. 2B). The above results demonstrate that PEMF treatment can upregulate expression of HO-1 gene expression, and thus reduce pro-inflammatory states via promotion of physiological processes related to degradation of pro-inflammatory heme.

PEMF Treatment of HDF, HEK and HMNC Cells Produces Cell- and Gene-Specific Increases in Transcript levels of Pro-Oxidant and Antioxidant Enzymes Pro-inflammatory ROS can be generated from a number of sources during the inflammation process. Given the importance of antioxidant enzymes in the removal of ROS, the effect of expression levels of antioxidant enzymes was investigated following PEMF treatment Expression levels of NADPH-oxidase (NOX), catalase (CAT), glutathione peroxidase-3 (GPX-3), glutathione reductase (GSR), superoxide dismutase-3 (SOD-3), and peroxiredoxin-6 (PRDX-6) mRNAs were assessed in HDF, HEK and HMNC cells relative to untreated cells, at 2 hours after treatment initiation of the PEMF treatment with a PROVANT device.

Figure 3:
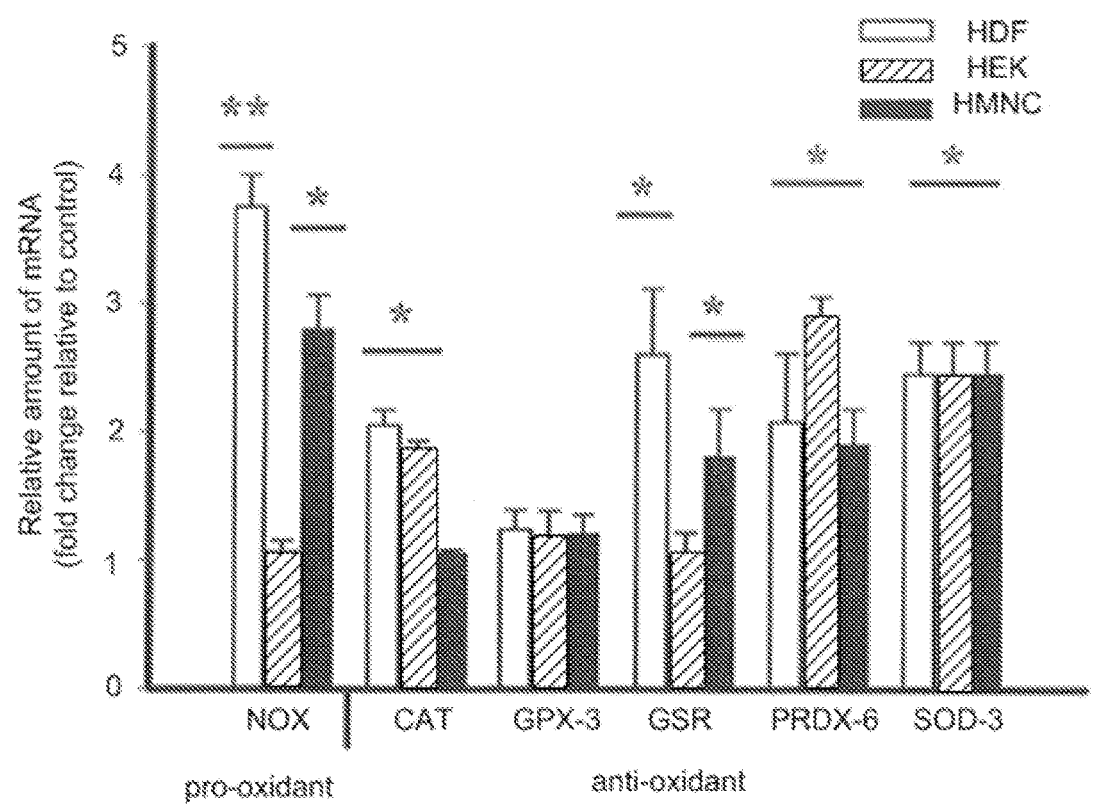
FIG. 3 illustrates the effects of PEMF treatment on the expression of various genes involved in certain pro-oxidant and anti-oxidant pathways in HDF, HEK, and HMNC cells.

Results are illustrated in FIG. 3. GSR transcript levels were increased in HDF and HMNC cells following PEMF treatment, while CAT transcript levels were increased in HDF and HEK cells after treatment. Expression of SOD-3 increased over 2-fold in all three cell types in response to PEMF treatment. In contrast, GPX-3 showed no increase in any of the three cell types following PEMF treatment compared to untreated cells. Interestingly, in addition to producing increased expression of the various antioxidant enzyme genes described above, PEMF treatment produced increased transcript levels of the pro-oxidant enzyme NOX in HDF and HMNC cells, though NOX expression remained unchanged in HEK cells following treatment.

PEMF Treatment of HDF, HEK and HMNC Cells Produces Changes in Transcript Levels of Enzymes Involved in Lipid Mediator Biosynthesis A number of metabolites of omega-3 and -6 polyunsaturated fatty acids, such as prostaglandins, leukotrienes, lipoxins, resolvins, protectins, and maresins, function as bioactive lipid mediators with important roles during both the acute and resolution phases of inflammation. Transcript levels of relevant enzymes following PEMF treatment 2 hours after initiation of PEMF treatment was measured.

The genes analyzed included cyclooxygenase 1 and 2 (COX-1 and COX-2, also known as prostaglandin-endoperoxidase synthase 1 and 2 (PTGS-1 and PTGS-2)), prostaglandin D2 synthase (PTGDS), prostaglandin E2 synthase (PTGES), prostaglandin I2 synthase (PTGIS), and arachidonate 5-, 12-, and 15-lipoxygenase (ALOX-5, ALOX-12 and ALOX-15).

Figure 4:
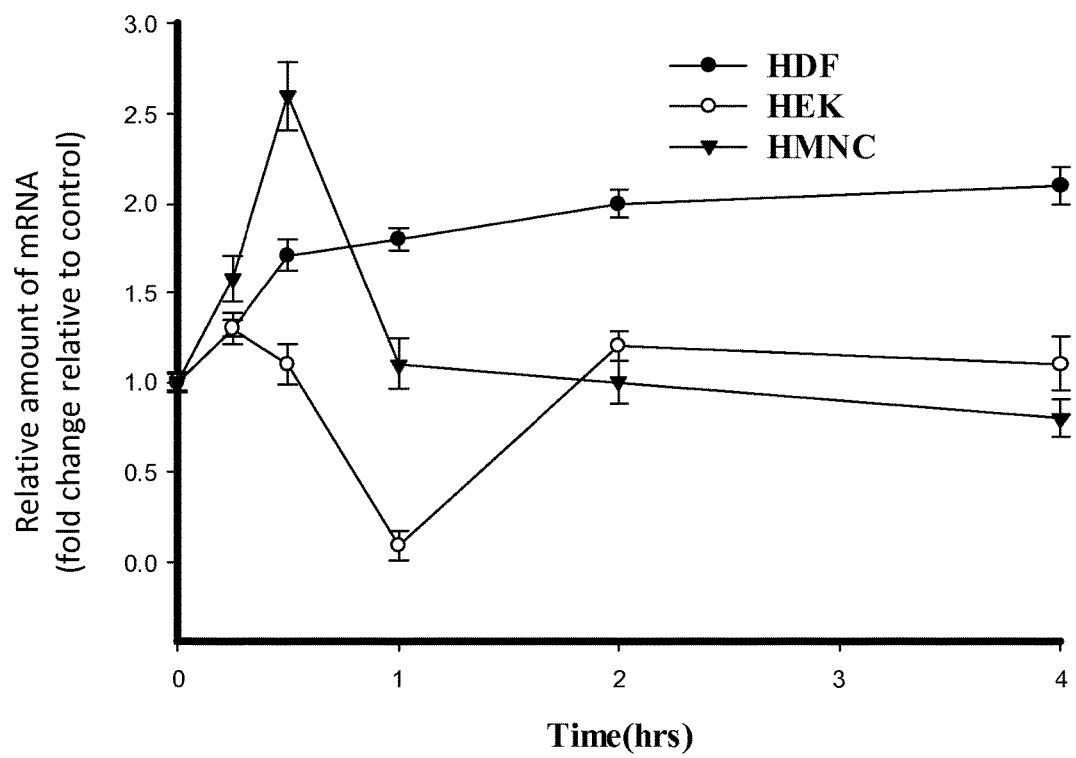
FIG. 4 illustrates the effect of PEMF treatment on the expression of COX-2 in HDF, HEK, and HMNC cells.

A preliminary gene expression analysis (FIG. 4) demonstrated a rapid rise increase in COX-2 transcript levels at 15 minutes following PEMF treatment for HDF, HEK, and HMNC cell types. This initial increase in COX-2 expression was followed by a subsequent decrease in COX-2 transcript levels in HEK and HMNC cells, while transcript levels remained elevated in HDF cells throughout the four hour time period evaluated.

Figure 5A:
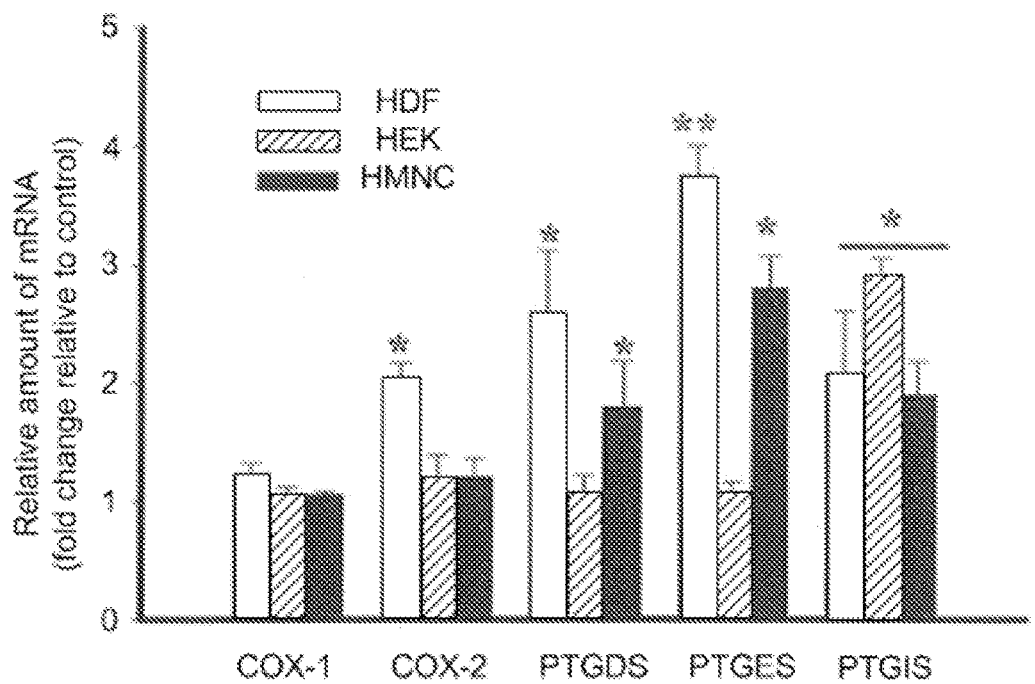
FIGS. 5A and 5B illustrate the effect of PEMF treatment on the expression of various genes believed to be involved in lipid mediator biosynthesis.
Figure 5B:
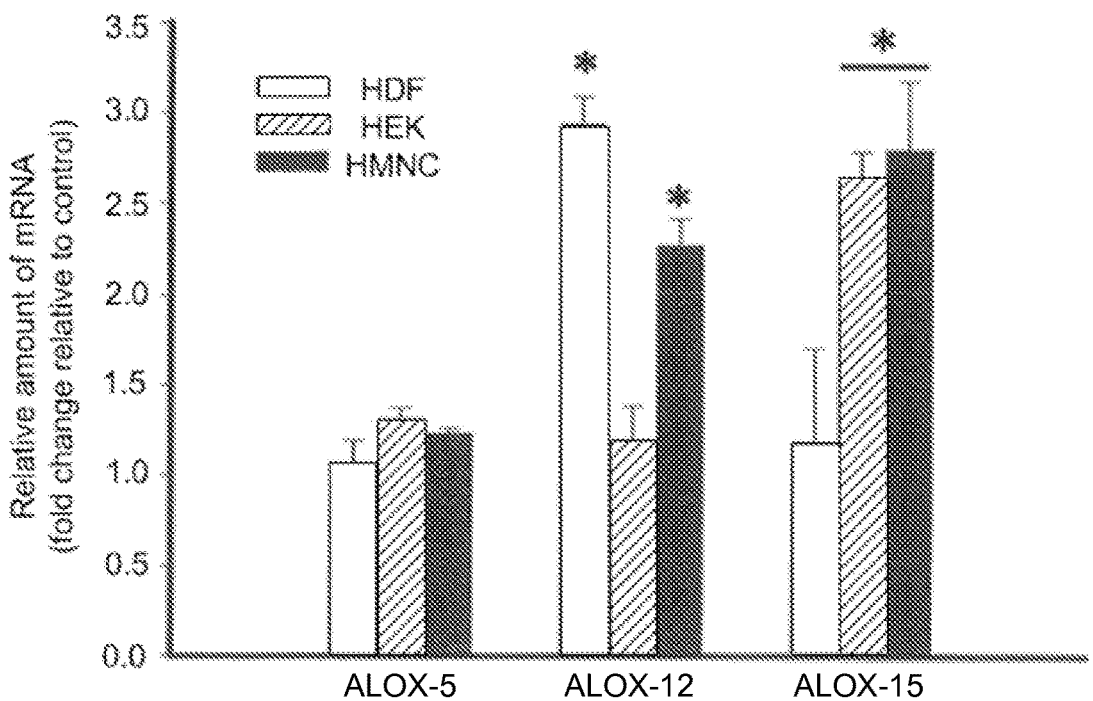

Results of cell specific response to PEMF treatment at 2 hours after initiation of treatment are shown in FIGS. 5A and 5B. Relatively little change in expression was observed for COX-1 expression levels in any cell type tested. COX-2 expression showed an increase in transcript levels in HDF cells only. Expression of PTGES demonstrated a strong response to PEMF treatment in HDF and HMNC cells, but expression was relatively unchanged for HEK cells. PTGIS was the only gene with expression demonstrating significant upregulated in HEK cells in the present study. Thus, while transcript levels of several prostaglandin synthases were upregulated in HDF and HMNC cells following PEMF treatment, only PTGIS expression was upregulated in HEK cells as shown in FIG. 5A.

FIG. 5B illustrates the effects of PEMF treatment on various lipoxygenase enzyme transcript levels in HDF, HEK, and HMNC cells at 2 hours after initiation of treatment. The results show that PEMF treatment of HDF, HEK, or HMNC cells did not produce any significant change in ALOX-5 levels in any of the three cell types studied. In contrast, transcript levels of ALOX-12 levels were significantly increased in HDF and HMNC cells in response to PEMF treatment (approximately 3.0 and 2.5-fold, respectively). In contrast, ALOX-15 levels increased approximately 3-fold in HMNC and HEK cells relative to untreated cells, with no change in expression in HDF cells.

The Effect of PEMF Treatment on Transcript Levels of Cytokines Involved in Pro- and Anti-Inflammatory Effects Cytokine-mediated effects on inflammation are often microenvironment-dependent, and can vary depending on other cytokines and regulatory molecules present. PEMF-associated changes in cytokine expression profiles were investigated.

Figure 6:
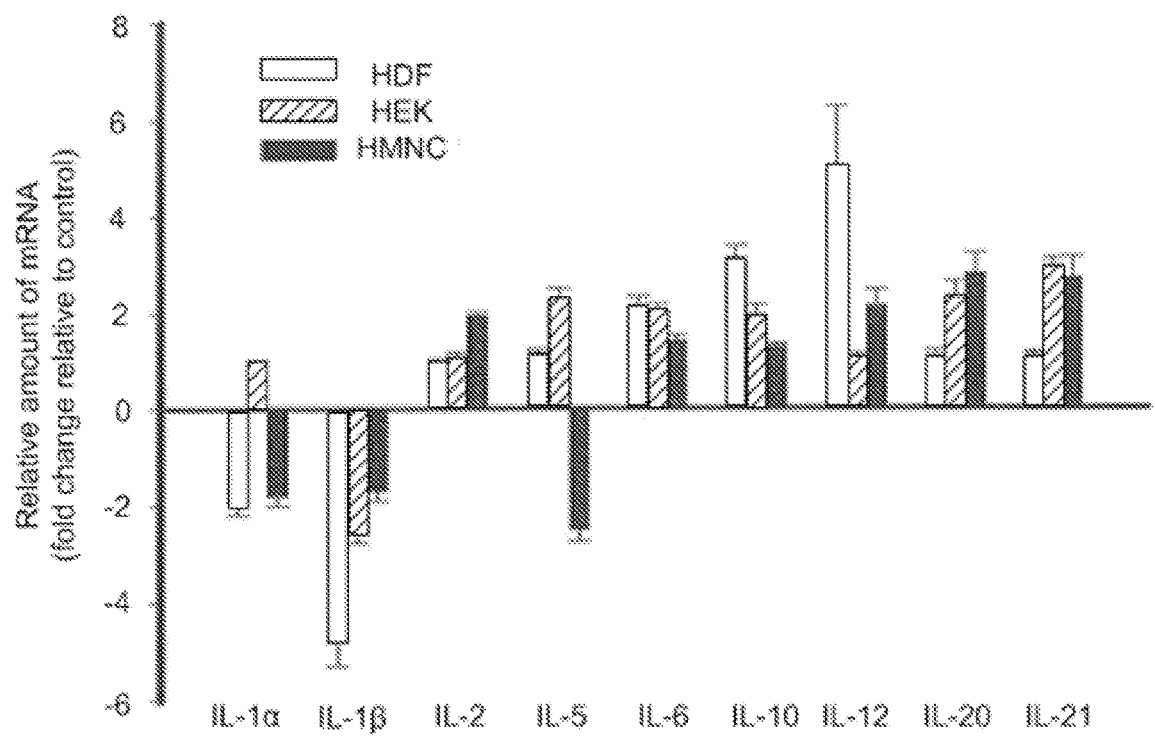
FIG. 6 illustrates the effect of PEMF treatment on the gene expression of various cytokine-related genes believed to be involved in certain inflammatory responses.

FIG. 6 illustrates the results of relative gene expression levels of several cytokines in HDF, HEK, and HMNC cells in response to PEMF treatment at 2 hours after initiation of PEMF treatment. The following cytokine transcripts were assessed: interleukin (IL) 1α, IL-1β, IL-2, IL-5, IL-6, IL-10, IL-12, IL-20, and IL-21.

Pertinently, IL-1β mRNA levels were lower in all three cell types following PEMF treatment. Other cytokines showed cell- and gene-specific responses in cytokine transcript levels following PEMF treatment. In particular, IL-1α transcript levels were lower in HDF and HMNC cells after PEMF treatment relative to untreated control cells, while expression levels in HEK cells was relatively unchanged. PEMF treatment produced upregulation of IL-2 expression in HMNC cells, while expression of these genes was unchanged in HDF and HEK cells. IL-5 transcript levels were increased in PEMF-treated HEK cells relative to untreated HEK cells. However, HMNC cells exhibited a decrease in IL-5 transcript levels. IL-12 expression was increased HDF and HMNC cells. Transcript levels of both IL-20 and IL-21 were upregulated in HEK and HMNC cells, while expression of these genes remained unchanged in HDF cells.

The results of this study illustrate that PEMF treatment may promote resolution of inflammation by stimulating gene expression of various inflammation dampening or pro-resolving inflammatory pathway mediators. Depending on the cell type, COX, additional downstream prostaglandin synthases, and ALOX were upregulated following PEMF treatment. These results are counter to the mechanism of action of pharmaceutical therapeutics such as non-steroidal anti-inflammatory drugs (NSAIDs).

Example 2

Gene Expression Panel Screening in Neuronal Cells to Identify PEMF Treatment-Responsive Genes, Pathways, and Indications An in vitro panel screening assay was performed to assess neuronal cell response to PROVANT in vitro PEMF treatment for the genes listed in Table 2. Neuroblastoma cells (IMR-32) where purchased from the American Type Culture Collection (Manassas, Va., USA; catalog number CCL-127). Culture media for cell cultures was purchased from VWR, Gibco, Sigma/Aldrich or Mediatech, Inc. (Herndon, Va., USA). Fetal calf serum, penicillin/streptomycin, trypsin, 1× phosphate buffered saline, sodium pyruvate, and non-essential amino acids were purchased from HyClone Laboratories, Inc. (now GE Healthcare Life Sciences, Inc., Logan, Utah, USA). IMR-32 cells were grown and maintained in a humidified incubator at 37° C. and 5% CO2.

Cultured IMR-32 cells were subjected to PEMF treatment using the PROVANT in vitro PEMF treatment conditions described above in Example 1. Likewise, cell harvest, total RNA isolation, and qRT-PCR were also performed as described above in Example 1. Results of the screening assay are summarized in Table 2.

TABLE 2

Summary of changes in transcript levels detected within 4 hours of PEMF treatment of IMR-32 cells relative to untreated control cells.

| | Increased | Decreased | No Effect |
| --- | --- | --- | --- |
| Heme oxygenases (HO-1, HO-2) | HO-1 | | HO-2 |

TABLE 2-continued

Summary of changes in transcript levels detected within 4 hours of PEMF treatment of IMR-32 cells relative to untreated control cells.

|  | Increased | Decreased | No Effect |
|---|---|---|---|
| Pro-oxidant enzymes |  | — | NOX |
| Anti-oxidant enzymes | SOD-3 | SOD-1 | GSR |
|  |  |  | PRDX-6 |
| Lipid mediator biosynthesis enzymes | | | |
| Prostaglandin synthesis enzymes | COX-2 |  |  |
|  | PTGDS |  |  |
|  | PTGES |  |  |
|  | PTGIS |  |  |
|  | COX-1 |  |  |
| Lipoxygenases | ALOX-12 |  | ALOX-5 |
|  | ALOX-15 |  |  |
| Interleukins |  | IL-1β | IL-20 |
|  | IL-5 | IL-1α | IL-26 |
|  | IL-6 |  |  |
|  | IL-10 | TNF |  |
|  | IL-12 |  |  |
|  | IL-21 |  |  |

Abbreviations: HO, heme oxygenase; NOX, NADPH-oxidase; CAT, catalase; GPX-3, glutathione peroxidase-3; GSR, glutathione reductase; PRDX-6, periredoxin-6; SOD-3, superoxide dismutase-3; COX-1 and -2, cyclooxygenase 1 and 2; PTGDS, prostaglandin D2 synthase; PTGES, prostaglandin E2 synthase; PTGIS, prostaglandin I2 synthase; ALOX, arachidonate lipoxygenase, IL, interleukin.

As evident in Table 2, PEMF treatment of IMR-32 cells produced differential patterns of gene expression for various inflammatory response pathway genes, with PEMF treatment producing increased expression of genes including HO-1, SOD-3, COX-1, COX-2, PTGDS, PTGES, PTGIS, ALOX-12, ALOX-15, IL-5, IL-6, IL-10, IL-12, and IL-21. In contrast, SOD-1, IL-1β, and TNF showed decreased expression in response to PEMF treatment. Expression of several genes, including HO-2, NOX, GSR, PRDX-6, ALOX-5, IL-20, and IL-26 did not show any response to PEMF treatment at the time point evaluated. Thus, PEMF treatment using the PEMF parameters described herein can produce a gene-specific pattern of modulation of transcriptional regulation, with upregulated, downregulated, and unmodulated expression of various inflammatory response pathway-related genes in response to PEMF treatment.

Example 3

Effects of PEMF Treatment on Gene Expression of Neuronal Cells

An in vitro study to evaluate the effects of PEMF treatment on neuronal cells was performed, with evaluation of changes in gene expression for genes involved in acute and resolution phases of the inflammatory response. Human IMR-32 neuroblastoma cell cultures were prepared as described above in Example 1. Cultured IMR-32 cells were subjected to PEMF treatment using the PROVANT in vitro PEMF treatment conditions described above in Example 1. Likewise, cell harvest, total RNA isolation, and qRT-PCR were also performed as described above in Example 1.

Figure 7:
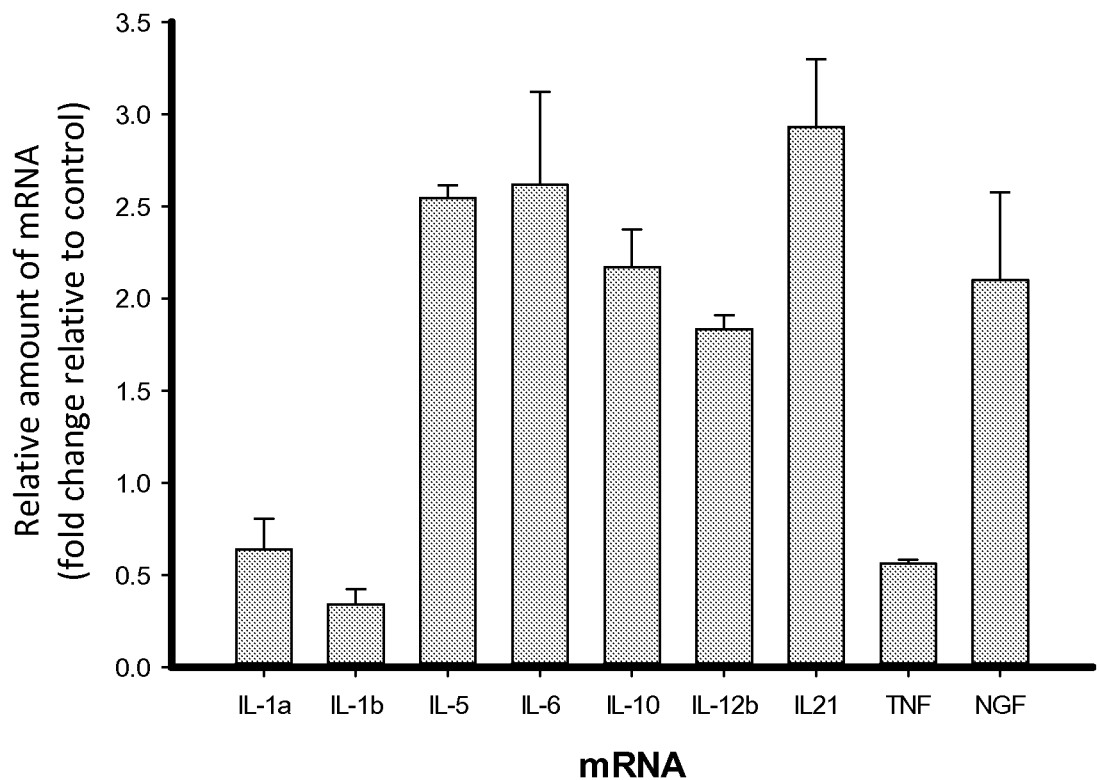
FIG. 7 illustrates the effect of PEMF treatment on expression of various genes including cytokine genes in IMR-32 cells.

FIG. 7 illustrates the results of an analysis of relative gene expression levels of several cytokines in IMR-32 cells in response to PEMF treatment at 2 hours after initiation of PEMF treatment. The following cytokine transcripts were assessed: interleukin (IL) 1α, IL-1β, IL-5, IL-6, IL-10, IL-12b, IL-21, TNF, and NGF. Pertinently, IL-1α, IL-1β, and TNF transcript levels were lower following PEMF treatment. The other cytokines evaluated, namely, IL-5, IL-6, IL-10, IL-12b, IL-21, and NGF, showed elevated gene expression levels following PEMF treatment.

Figure 8:
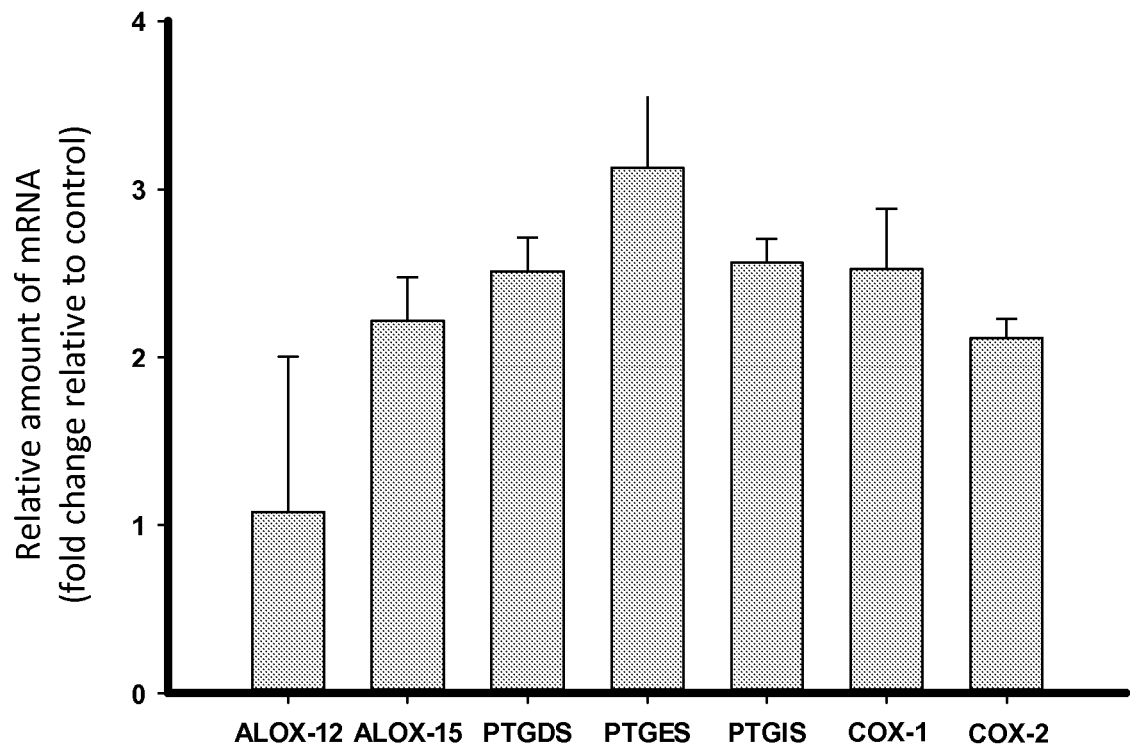
FIG. 8 illustrates the effect of PEMF treatment on expression of various genes including COX and ALOX genes in IMR-32 cells.

FIG. 8 illustrates the effects of PEMF treatment on expression of COX and ALOX genes in IMR-32 cells. ALOX-12 expression was unchanged following PEMF treatment. ALOX-15, PTGDS, PTGES, PTGIS, COX-1, and COX-2 showed increase gene expression in response to PEMF treatment.

Figure 9:
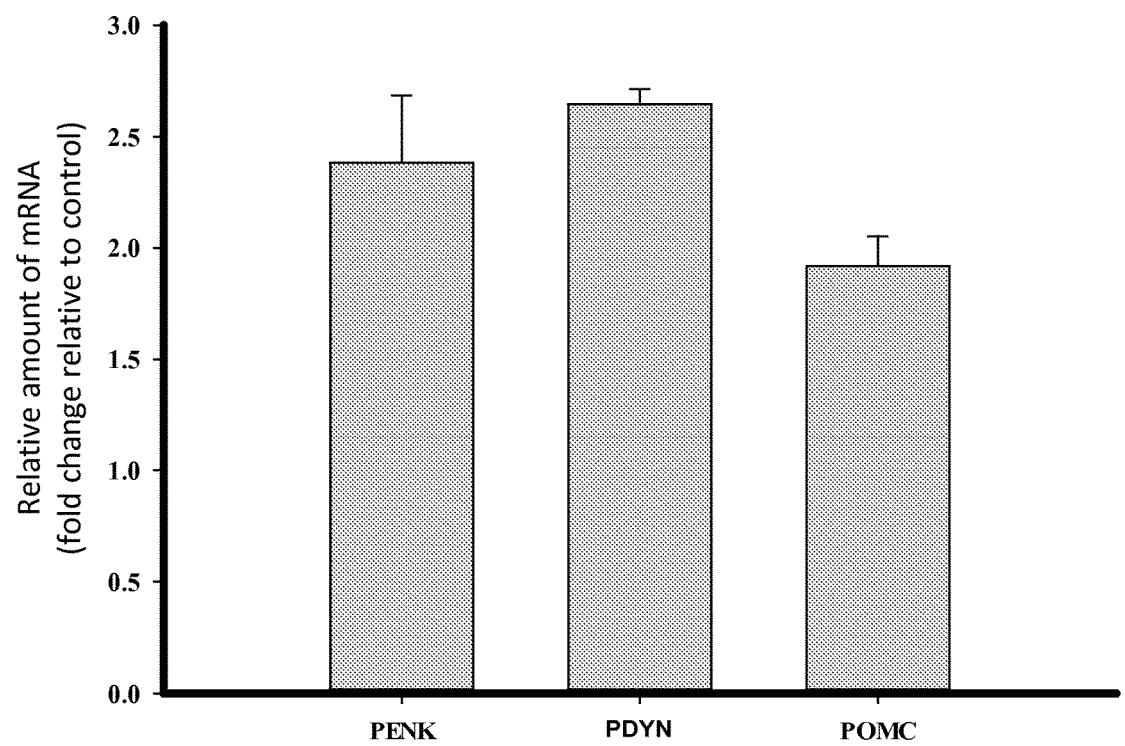
FIG. 9 illustrates the effect of PEMF treatment on expression of various endogenous opioid genes in IMR-32 cells.

FIG. 9 illustrates the effects of PEMF treatment on expression of endogenous opioid genes in IMR-32 cells. Transcript levels for each of PENK, PDYN, and POMC genes in IMR-32 cells were upregulated in response to PEMF treatment of the cells.

Example 4

PROVANT Therapy Influence on Pain Sensitivity (Four Subject Study)

A double-blind, randomized, sham-controlled study was performed using PROVANT Therapy to test the effect of PEMF treatment on pain sensitivity to different qualities of experimentally induced pain in healthy pain-free human subjects. The study also evaluated the effect of PROVANT Therapy dosage time (30 minutes and one hour) on pain sensitivity.

Methods

Four healthy pain free subjects participated. Pain threshold to thermal stimuli and pressure were obtained from the non-dominant forearm and measured at baseline and after 30 and 60 minutes of active or sham PROVANT Therapy treatment using four standardized experimental pain measures set forth below. Assessment of pain thresholds to different known and controlled thermal and pressure stimuli were obtained. Re-assessment of experimental pain measures occurs after the 30 minute treatment in the same order as at baseline and after a further 30 minutes of treatment. The use of well-controlled experimentally-induced pain paradigms in healthy pain-free subjects provides a useful and simple translational research paradigm with which to understand specific analgesic and dosing effects of PROVANT Therapy.

In this four subject study, two subjects received active Provant Therapy treatment (Active1 and Active2) and two subjects received sham (Sham1 and Sham2). Four tests were conducted: Cuff Pressure Pain Threshold, Mechanical Pain Threshold, Submaximal Effort Tourniquet Test (SMET) and Hand Grip Strength, and Cold Pressor Pain Threshold. Details of these four tests are described below.

Experimental Pain Tests

Each of the following experimental pain stimuli were applied and measures of pain threshold were obtained, at baseline, after 30 minutes (First Test) and 60 minutes (Second Test) of active or sham treatment.

Cuff Pressure Pain Threshold was measured with a standard blood pressure cuff. The cuff was applied to the non-dominant forearm. It was inflated at a steadily increasing rate until subjects were unwilling to withstand any further increase in pressure (pain tolerance).

Mechanical Pain Threshold was measured using a hand-held pressure algometer (dolorimeter) with a 1 cm$^2$ digital probe applied at a rate of 1 kg/sec. The probe was applied perpendicular to the skin, on the mid-forearm on anterior surface. A steady increase in pressure was applied at approximately 1 kg/sec and the subject responded when the subjects were unwilling to tolerate any further increase in pressure (pain tolerance).

Tonic Pain Stimuli

Submaximal Effort Tourniquet Test (SMET) and Hand Grip Strength is a tonic test of ischemic pain and simultaneous hand grip strength. For this test a blood pressure cuff was applied to the arm but not inflated. Maximal hand grip force was measured using a hand-held grip dynamometer. The cuff was inflated to about 200 mm Hg and maintained. The subject made a fist and relaxed a hand at about a rate of about 1 cycle per second. Pain tolerance was defined as the length of time the participant was willing to withstand the pressure. Subjects were informed that the procedure would be stopped after 5 minutes if they had not reached tolerance.

The Cold Pressor Pain Threshold and Tolerance (Cold) is a tonic test of pain tolerance to cold. The procedure was completed using an insulated water cooler filled with water and ice of sufficient depth to allow for full immersion of the non-dominant forearm and hand. The water temperature was maintained between 1° C. and 5° C. Subjects were instructed to place their right hand into the cold water up to their wrist and to leave it submerged until they are no longer able to tolerate the pain. Additionally, subjects kept their hand open rather than making a fist whilst in the water. The length of time the subject's hand remained underwater was recorded. Subjects were informed that the cold pressor procedure would be stopped after 5 minutes if they had not reached tolerance.

PROVANT Therapy Intervention

Subjects were randomly assigned to receive active or sham PROVANT Therapy treatment to their non-dominant forearm by a research assistant blind to the type of device (active or sham). The active and sham devices were identical except for a designated code which was known only to the principal investigator. For the intervention, subjects simply rested their forearm on a rubberized pad and the device was turned on. A 30 minute timer was visible to the subject and research assistant. Subjects did not perceive any sensation from the PROVANT Therapy as it is a subthreshold intervention.

Data Analysis

Data for each of the four tests performed and each of the four study subjects is presented graphically in FIGS. 10A-10D. The results are described in more detail below.

Results

Cuff Pressure Pain Threshold

Figure 10A:
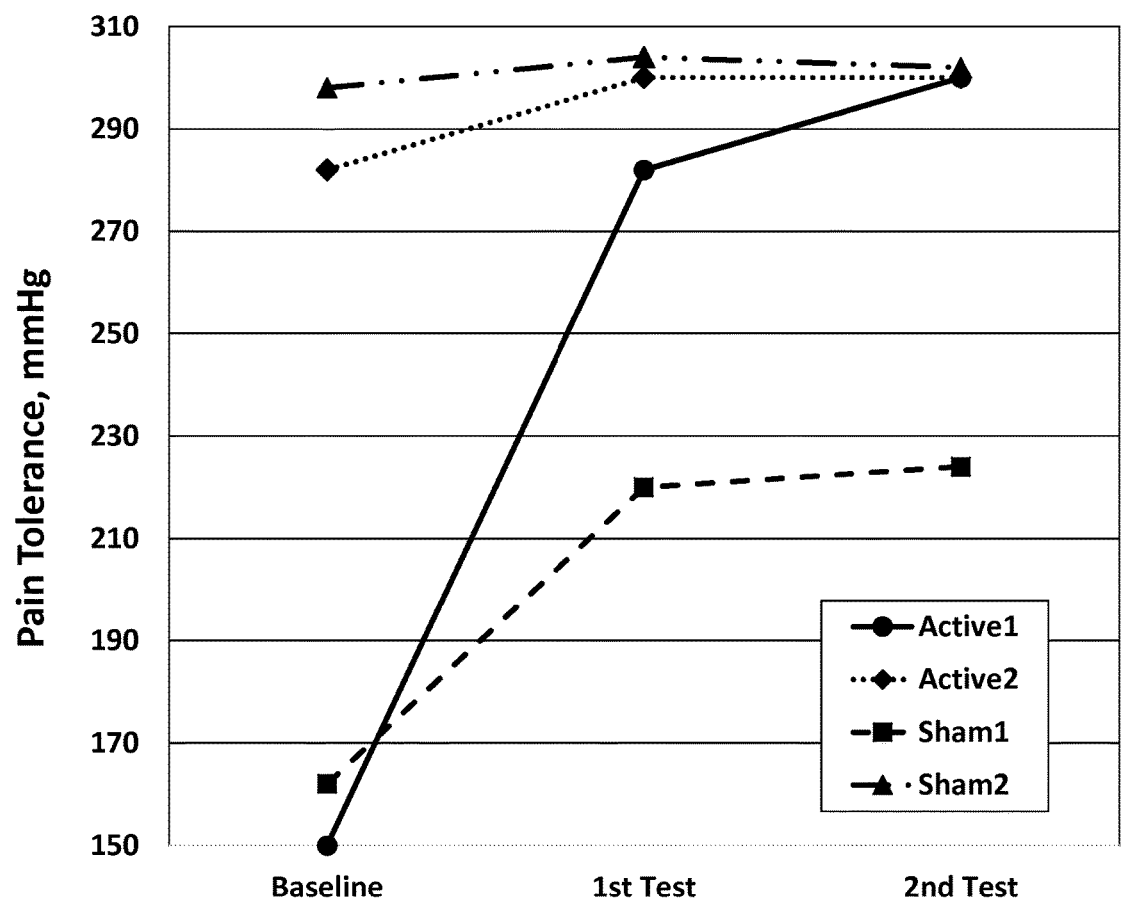
FIGS. 10A-10D illustrate the results of a clinical evaluation of the effects of PEMF treatment on pain tolerance.

Graphic representation of the results for each of the four subjects is provided in FIG. 10A. Two subjects (Active1 and Sham1) reported baseline pain scores around 150 mmHg cuff pressure while two subjects (Active2 and Sham2) reported baseline pain at near maximum pressure limit. Those subjects with baseline scores near maximum pressure limit "maxed out" at the 2nd assessment. Both Active1 and Active2 showed an increased cuff pressure tolerance at the 2nd assessment compared with baseline and Active1 also showed an incremental increase at the 3rd assessment. Sham1 had an increased pressure tolerance for the 2nd assessment but not the 3rd assessment.

Discussion: Historically, most subjects report pain threshold near 150 mmHg. These results demonstrate two distinct groups. Active1 and Sham1 reported baseline threshold pain within normal limits. Active1 exhibited a dose response improving with each PEMF exposure; while Sham1 showed an increased pain threshold after the first "treatment" but not the second treatment. Active2 and Sham2 appear to be reporting results more consistent with maximal tolerated pain, in which case, emotional and cognitive control are used to override sensory pain input to allow the subject to report higher pressure tolerance. It is difficult to determine the ultimate influence of PEMF and/or Sham on pain for these subjects since the upper pressure limit for the trial has been breached.

Mechanical Pain Threshold

Figure 10B:
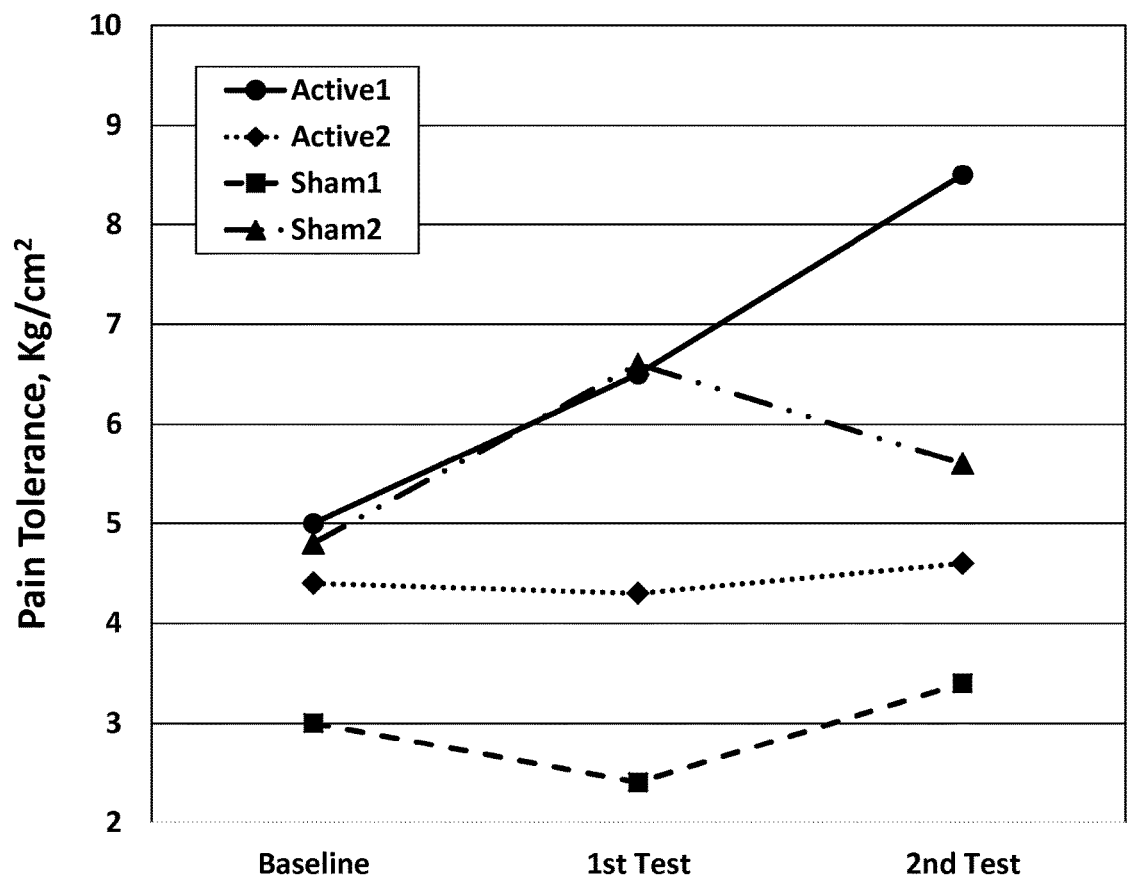

Graphic representation of the results for each of the four subjects is provided in FIG. 10B. Active1 demonstrated an increase in focal pressure tolerance at 2nd and 3rd assessment while Active2 did not increase significantly at 2nd or 3rd assessment. Sham1 had a decrease in tolerance at 2nd assessment with a slight improvement over baseline at 3rd assessment while Sham2 had an increase at 2nd assessment which dropped back to near baseline at the 3rd assessment.

Discussion: Active1 showed a positive dose response at both 2nd and 3rd assessment. Active2 showed a very slight increase to this stimulus at 2nd or 3rd assessment and would be considered a "non-responder" in this test session. Sham1 was able to increase the threshold after the first treatment sessions; however, the reported pain threshold returned to baseline at the 3rd assessment. Sham2 had an overall slight improvement over baseline at the 3rd assessment after an initial drop in threshold at the 2nd assessment.

Submaximal Effort Tourniquet Test (SMET)

Figure 10C:
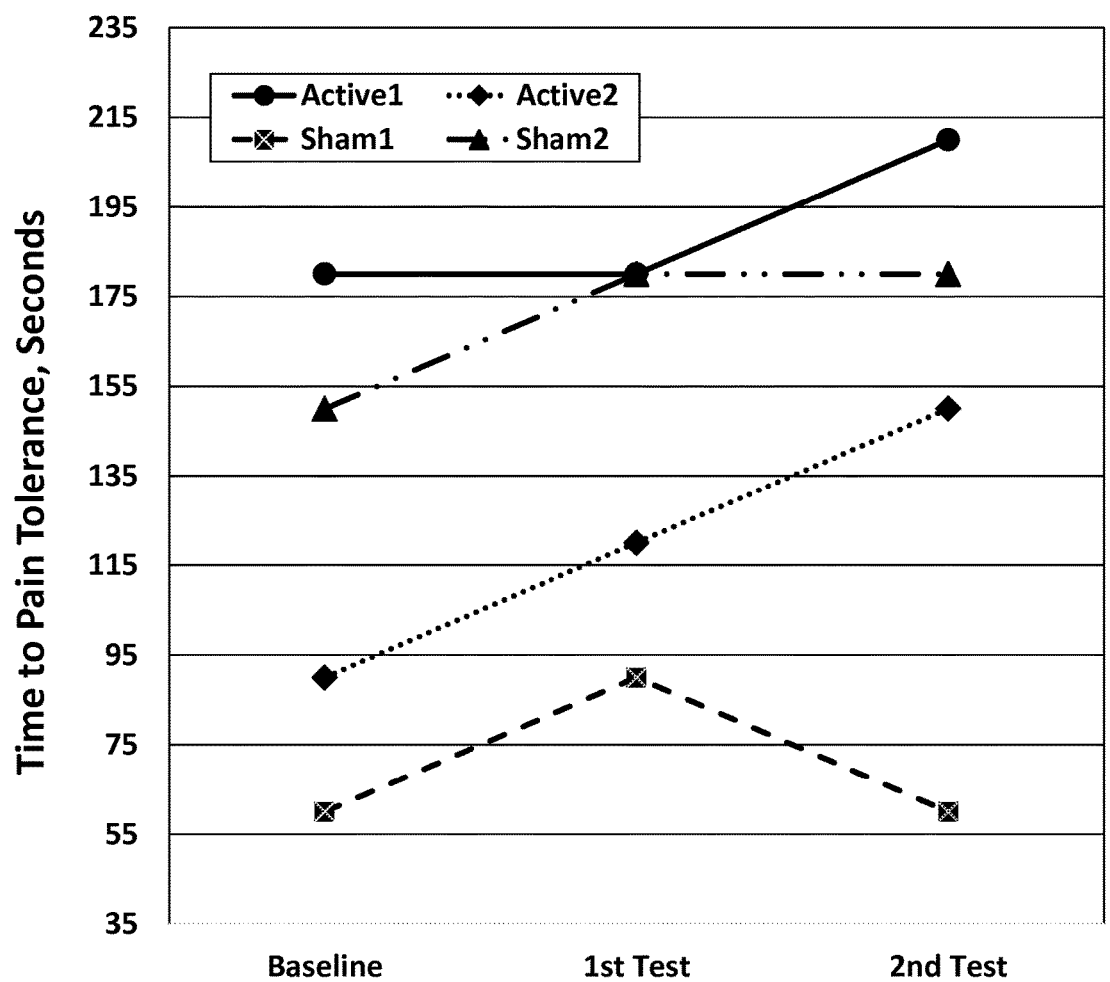

Graphic representation of the results for each of the four subjects is provided in FIG. 10C. Both Active1 and Active2 show an increased time to pain tolerance during maximal grip strength at 2nd and 3rd assessments; while both Sham1 and Sham2 demonstrated an increase in duration of time holding the maximal grip at 2nd but not the 3rd assessment time. In fact, Sham1 showed a significant decrease in ability to maintain grip strength compared to baseline.

Discussion: This test pairs a functional outcome assessment (grip strength) with the controlled stressor ischemia using a suboptimal pressure tourniquet. The subjects become more ischemic with time which should affect the subject's maximal grip strength. Active1 and Active2 demonstrated increased time to maximal tolerable pain at 3rd assessment compared with baseline. Comparatively, Sham1 and Sham2 showed a plateau or decreased time to maximal tolerable pain at 3rd compared with 2nd assessments.

Cold Pressor Pain Threshold

Figure 10D:
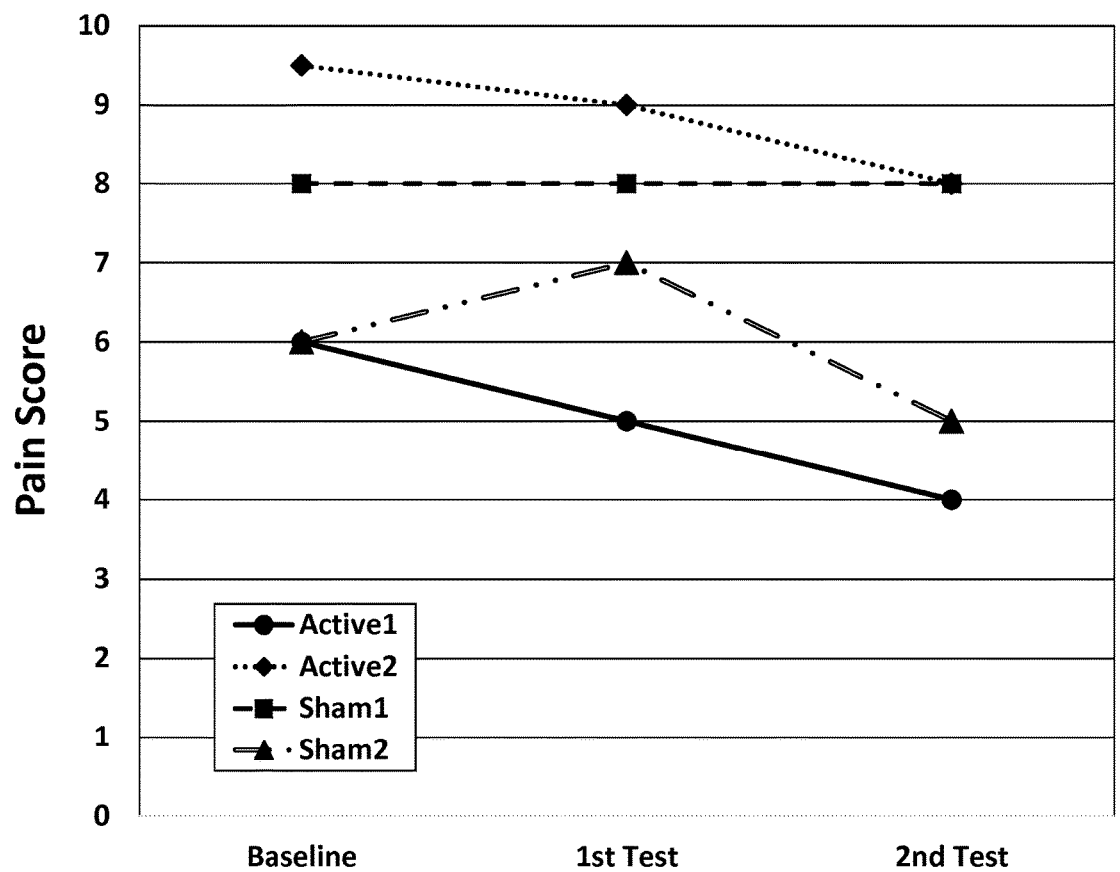

Graphic representation of the results for each of the four subjects is provided in FIG. 10D. Active1 reported a moderately low baseline score and demonstrated a subsequent linear decrease in pain at 2nd and 3rd assessments. Active2 reported a near maximal pain score at baseline and also reported a near linear decrease in score at 2nd and 3rd assessments. Sham1 noted a high baseline score with no change at 2nd and 3rd assessments; while Sham2 had a moderate initial score that worsened at 2nd assessment and decreased at the 3rd assessment.

Discussion: This session used known painful stimuli to assess subject's perception of the severity at baseline. Decreases in the pain score are considered improvements. The longer the duration of exposure to this stimulus, the more likely the subject was to experience a progressive decrease in pain secondary to the numbing effect of the ice bath. Both Actives showed a strong dose response to PEMF; while the Sham subjects showed a "non-response" to minimal change.

Example 5

PROVANT Therapy Influence on Pain Sensitivity

A double-blind randomized sham controlled study is performed using the PROVANT device to test the effect of PEMF treatment on pain sensitivity to different qualities of experimentally induced pain in healthy pain-free human subjects. The study will also evaluate the effect of the PROVANT device dosage time (30 minutes and one hour) on pain sensitivity.

A population of 40 healthy pain free subjects between the ages of 22 and 65 are recruited. Pain threshold and tolerance to thermal stimuli and pressure are obtained from the non-dominant forearm and measured at baseline and after 30 and 60 minutes of active or sham PROVANT device treatment using five standardized experimental pain measures set forth below. Assessment of pain thresholds and tolerance to different known and controlled thermal and pressure stimuli are obtained in a counterbalanced order, with the exception that cold water tolerance assessed last. Subjects are randomized to receive PROVANT device treatment with active or sham PROVANT device. Re-assessment of experimental pain measures occurs after the 30 minute treatment in the same order as at baseline and after a further 30 minutes of treatment. The use of well-controlled experimentally-induced pain paradigms in healthy pain-free subjects provides a useful and simple translational research paradigm with which to understand specific analgesic and dosing effects of the PROVANT device.

Experimental Pain Tests

Each of the following experimental pain stimuli are applied in a counterbalanced order and measures of pain threshold or tolerance is obtained as appropriate, at baseline (TO), after 30 minutes (T1) and 60 minutes (T2) of active or sham treatment.

Cuff Pressure Pain Threshold is measured with a standard blood pressure cuff. The cuff is applied to the non-dominant forearm. It is inflated at a steadily increasing rate until the stimulus becomes "just painful" (pain threshold) and when the subjects are unwilling to withstand any further increase in pressure (pain tolerance).

Mechanical Pain Threshold and Tolerance is measured using a hand-held pressure algometer with a 1 $cm^2$ digital probe applied at a rate of 1 kg/sec. The probe is applied perpendicular to the skin, on the mid-forearm on anterior surface. A steady increase in pressure is applied at approximately 1 kg/sec and the subject responds when the stimulus intensity becomes 'just painful" (pain threshold) and when the subjects are unwilling to tolerate and further increase in pressure (pain tolerance).

Thermal Pain Threshold to Heat and Cold is measured using the QST system. Contact thermal stimuli are delivered using a computer-controlled Medoc Thermal Sensory Analyzer (TSA-II; Ramat Yishai, Israel) through a 30 $mm^2$ contact thermode. From a baseline temperature 32° C., the temperature of the thermode gradually rises or falls at a rate of 1° C./s. When activated by the subject as pre-directed for pain threshold, the response device simultaneously records the temperature of the thermode and returns the temperature to its baseline value. The thermode has a preset maximum and minimum cut-off temperature level (50° C. and 0° C., respectively). If the probe temperature reaches the preset levels without a subject response, the system reduces temperature to the preset baseline of 32° C. by active cooling at a rate of 10° C. per second. Three trials for each measure of pain threshold is recorded and the average will be used as the dependent variable.

Tonic Pain Stimuli

Cold Pressor Pain Threshold and Tolerance (Cold)

The cold pressor procedure is a tonic test of pain tolerance to cold. The procedure is completed using an insulated water cooler filled with water and ice of sufficient depth to allow for full immersion of the non-dominant forearm and hand. The water temperature is maintained between 1° C. and 5° C. Subjects are instructed to place their right hand into the cold water up to their wrist and to leave it submerged until they are no longer able to tolerate the pain. Additionally, subjects keep their hand open rather than making a fist whilst in the water. Several measures will be taken during the procedure, including pain threshold, pain tolerance, and pain ratings. Subjects rate their pain intensity on a numerical (0-10) scale on initial submersion and every 15 seconds while their hand is underwater. In addition, subjects provide final pain intensity ratings at tolerance (FRIN), just as they remove their hand from the cold water. The length of time the subject's hand remains underwater is recorded. Subjects are informed that the cold pressor procedure will be stopped after 5 minutes if they have not reached tolerance.

Submaximal Effort Tourniquet Test (SMET) and Hand Grip Strength:

This is a tonic test of ischemic pain and simultaneous hand grip strength. For this test a blood pressure cuff is applied to the arm but not inflated. Maximal hand grip force is measured using a hand-held grip dynamometer. The cuff is inflated to about 200 mm Hg and maintained. The subject makes a fist and relaxes at about a rate of about 1 cycle per second. Several measures will be taken during the procedure, including pain threshold, pain tolerance, and regular pain ratings. Subjects rate their pain intensity on a numerical (0-10) scale about every 30 seconds while the cuff is inflated and while applying maximal grip strength to the hand-held dynamometer. In addition, subjects provide final pain intensity ratings at tolerance (FRIN) or at 5 minutes (whichever comes first) and grip strength is measured just before the cuff is deflated. Pain threshold is the time at which the subject first reports pain. Pain tolerance is defined as the length of time the subject is willing to withstand the pressure. Subjects are informed that the procedure will be stopped after 5 minutes if they have not reached tolerance.

PROVANT Therapy

Subjects are randomly assigned to receive active or sham PROVANT device treatment to their non-dominant forearm by a research assistant blind to the type of device (active or sham). The active and sham devices are identical except for a designated code which is known only to the principal investigator. For the intervention, subjects simply rest their forearm on a rubberized pad and the device is turned on. A 30 minute timer will be visible to the subject and research assistant. A new pad cover will be used after each 30 minute application. Subjects will not perceive any sensation from the PROVANT Therapy as it is a subthreshold intervention.

Experimental Procedure

The order of experimental pain tests for baseline measures is randomized for each subject with the exception that the cold pressor test conducted last. This same order of testing will be used after each 30 minute PROVANT Therapy intervention.

Data Analysis

Data is summarized by means with standard deviations and medians with minimum and maximum values. Summary statistics of pain threshold and pain tolerance are stratified by group, stressor, and time point. In addition, group, mean pain ratings over time for each tonic pain stressor (SMET and Cold Pressor) are plotted and visually assessed. The primary analysis to assess the effectiveness of PROVANT Therapy will use a general linear model with repeated measures MANOVA.

Example 6

A Single-Center, Randomized, Sham-Controlled, Double-Blind Study of PROVANT Therapy to Evaluate Small Fiber Nerve Growth and Function in Subjects with Painful Peripheral Diabetic Neuropathy A single-center, randomized, double-blind, sham-controlled clinical trial is conducted on subjects with painful peripheral diabetic neuropathy (PPDN) in at least one foot. Eligible subjects include those between 22 and 80 years of age with Type 2 diabetes having persistent numbness, tingling, or burning in at least one foot despite treatment and with positive provocative sign and positive Tinel's sign. Eligible subjects are randomized in a 2:1 ratio to receive PROVANT device treatment with an active PROVANT device or an identical inactive sham device. Subjects treat at home twice daily for 60 days.

Changes in nerve density, nerve function, and skin perfusion after 60 days of treatment is evaluated. Nerve density is evaluated via examination in histopathologic/histochemical changes to the skin biopsies from baseline to Day 61. Nerve function is evaluated by assessment of the changes in Sympathetic Skin Response (SSR) and Nerve Conduction Velocity (NCV) testing between baseline and Day 61. Skin perfusion is measured by assessment of Skin Perfusion Pressures (SPP) at baseline and at Day 61. Evaluation criteria, including SSR, NCV, and SPP, are explained in more detail in the following sections.

Evaluation Criteria

Skin Biopsy: To assess c-fiber or a-fiber nerve density at or near the site of treatment with PROVANT Therapy. At Day 0 Visit, a biopsy is obtained from the dorsal aspect of the index foot within 1 cm distal (caudal) to the web between the hallux and 2nd toe. The area is washed with alcohol. Then a small amount of local anesthetic (lidocaine) is injected just under the skin. After the skin is numb, a 3 mm punch biopsy is performed. The biopsy is sent to a histopathology lab for assessment of nerve density. At the Day 61 Visit, a second biopsy is obtained at a different spot on the dorsal aspect of the index foot within 2 cm lateral to the initial biopsy.

Sympathetic Skin Response (SSR): SSR is a non-invasive test to measure nerve function. SSR can be used to evaluate nerve function for small fiber peroneal nerve branches. Skin electrodes are placed on the back and sole of the foot. A small electrical stimulation is used to activate the nerve on the back of the foot, and the response is measured by the electrode on the sole. The electrical stimulus may be repeated to acquire consistent results. The amplitude (in mV) and time to onset (in msec) is measured for the resulting wave form. Increases in amplitude and decreases in time to onset are indicative of improvement in nerve function.

Nerve Conduction Velocity (NCV): To evaluate nerve function for large myelinated nerve fibers, an active electrode is placed on the extensor digitorum brevis (EDB) and a reference electrode is placed on the index foot great toe. A measurement of 8 cm from the active electrode towards the anterior aspect of the ankle is taken and marked with a pen. Gradual electric stimulation, which increases in mA, is performed at the marked site until the wave form has reached the maximum amplitude.

The next stimulation is performed at the common peroneal nerve at the fibular tunnel using the same technique as the deep peroneal nerve. Following this, the peroneal nerve will be stimulated at the popliteal fossa. Measurements are taken from each stimulation site which is then recorded to obtain the latency.

The same stimulation technique is used for the tibial nerve. The active electrode is placed on the abductor halluces and the reference electrode is placed on the 5th toe of the index foot. Measurement of 8 cm from active electrode towards the "tarsal tunnel" area is taken and marked with a pen. Gradual electric stimulation, which increases in mA, is performed at the marked site until the wave form has reached the maximum amplitude.

For each of the assessments above, the maximum amplitude of the resultant wave form is recorded. Additionally, the time to onset of the resultant waveform is recorded.

An additional stimulation is performed at the popliteal fossa making note of how the foot is responding to ensure that the correct nerve is being stimulated. Measurements are taken from each stimulation site which is then used to record latency.

Skin Perfusion Pressures (SPP): Measures pressure (in mm Hg) of microcirculation using a laser Doppler sensor. Subject lies down in supine position and remains silent and still. The Laser Sensor Assembly (LSA) is inserted into the LSA Placement Guide and the optical sensor window is oriented toward the skin. The LSA is placed on the dorsal aspect of the foot within 2 cm, but no closer than 1 cm, of the location of the planned biopsy. The SPP will be obtained prior to the skin biopsy. A cuff is positioned so that the LSA is centered on the bladder both horizontally and vertically. The pressure of the cuff is then automatically increased to a pressure necessary to occlude blood flow and then released at a controlled rate and a measurement of the pressure in the angiosome is made. SPP (mmHg) at reactive hyperemia is recorded. A second measure of SPP will be obtained on the plantar aspect of the foot directly below the location where the SPP was performed on the dorsal aspect of the foot.

Study Procedures

Subjects are evaluated for non-myelinated sympathetic nerve response using the SSR method. A 3 mm punch skin biopsy is obtained on the dorsal aspect of the foot most affected by peripheral neuropathy. The biopsy is obtained in the area between the hallux and the second toe to represent small fiber innervation emanating from the deep peroneal nerve. NCV is performed specifically to assess the activity of the deep peroneal nerve. Measurement of local SPP is assessed on the dorsal and plantar surfaces of the index foot.

Subjects are randomized 2:1 to receive either therapy using an active PROVANT device or a sham control "treatment" using an identical but inactive sham device. Subjects self-treat twice daily (morning and evening; e.g., 8 am±2 hours and 8 pm±2 hours) for 60 days at home. Subjects record daily pain scores based on a 10 point numerical pain score scale.

After 60 days of treatment, subjects have provocative sign and Tinel's sign evaluated, and SSR, NCV, and SPP tests conducted, and a 3 mm punch biopsy obtained.

For analysis of the data, the last pre-treatment observation is used as baseline for calculating post-treatment changes from baseline. All confidence intervals will use a significance level of 5%. The changes from baseline are summarized for SSR, NCV, biopsy, and SPP results. The mean percent change from baseline is calculated for each treatment group and 95% confidence intervals constructed.

Example 7

A Single-Center, Randomized, Sham-Controlled, Double-Blind Study of PROVANT Therapy to Evaluate Angiogenesis in Subjects with Postoperative Diabetic Peripheral Neuropathic Wounds A single-center, randomized, double-blind, sham-controlled clinical trial is conducted on subjects with diabetic peripheral neuropathic wounds that are undergoing regular debridement. Eligible subjects include those between 22 and 80 years of age with Type 1 or Type 2 diabetes having a diabetic foot wound that has undergone standard therapy for at least 30 days without significant improvement in wound size, exudate, tissue composition or pain resolution. Eligible subjects are randomized to receive PROVANT device treatment with an active PROVANT device or a sham device. Subjects are randomized in a 2:1 ratio (e.g., 8 active: 4 sham) using a computer-generated scheme based on a permuted block algorithm.

Subjects self-treat at home twice daily for 90 days or until the wound has undergone about 100% re-epithelialization, whichever occurs first.

Subjects undergo weekly evaluations in the clinic to assess pain management and wound healing progression in addition to their rate of angiogenesis based upon Novadaq microvascular scanning using a fluorescence dye. Subjects undergo a final evaluation at completion of their treatment.

Changes in microvascular perfusion, rate of wound closure, and wound associated pain are assessed at the time of wound closure or 90 days, whichever occurs first. Angiogenesis is evaluated through observations of microvascular parameters as recorded by angiography using Novadaq scanning technology. Wound closure is evaluated by plotting weekly wound healing trajectories over time using wound volume measurements and photographic (Silhouette® Camera) documentation tracking wound volume changes from Baseline and during the weekly visits. Wound pain is plotted over time to create a pain trajectory using average weekly pain scores derived from an 11-point Numeric Pain Rating Scale (0-10), comparing baseline to Day 91. The functional assessment score is obtained every 4 weeks using the Patient-Specific Functional Scale comparing baseline to Day 91.

Study Procedures

Several efficacy outcome measures will be assessed in order to allow for characterization of the response to PEMF therapy, including the following:

Microvascular Angiogenesis and Perfusion Response (MAPR): LUNA™ scans are conducted at each weekly visit to evaluate perfusion via influx blood flow, peak flow, and efflux blood flow at the area of interest. Change in measurement from baseline is assessed. Analyses will include total wound area perfusion, perfusion in the wound margin, and perfusion in the wound bed.

Wound Healing Response (WHR): Wound assessment will be conducted during the weekly clinic visits using the Silhouette® 3-D volumetric camera. Silhouette® calculates the area, depth, and volume and tracts the healing progress over time.

Pain Intensity (PI): A validated 11-point Numerical Pain Rating Scale (NPRS) with scores (0-10) collected as patient reported outcomes on a daily diary. Pain Intensity (PI) will be assessed each morning by the subject immediately following the morning PROVANT device treatment session during the 90 day treatment period. A reduction of 2 points or 30% from baseline is considered a clinically meaningful change in PI.

Functional Assessment: A validated functional assessment using an 11-point scale for each activity on the Patient-Specific Functional Scale with scores (0-10) collected as patient reported outcomes at the enrollment visit and every 4 weeks thereafter. Subjects self-identify 3 to 5 daily activities that they are unable to do or have difficulty completing and rate their ability to complete each activity. A reduction of 2 points from baseline is considered the minimum detectable change (90% Confidence Interval) for the average score. A reduction of 3 points from baseline is considered the minimum detectable change (90% Confidence Interval) for a single activity score.

Subject adherence (compliance with twice daily treatment with the study device) is also assessed.

What is claimed is:

1. A method of modulating one of a peroneal nerve and a tibial nerve function in a patient in need thereof comprising:
   administering a PEMF treatment to the patient, the PEMF treatment comprising applying the PEMF treatment to a treated foot of the patient with a pulse frequency of about 1000 Hz and a pulse width of about 42 µs;
   producing one of an increase in sympathetic skin response (SSR) waveform amplitude, a decrease in SSR time-to-onset, and an increase in nerve conduction velocity in the treated foot by administering the PEMF treatment; and
   producing an increase in expression of one of IL-5, IL-6, IL-10, IL-12b, IL-21 and NGF genes in a neuronal cell in the treated foot by administering the PEMF treatment;
   wherein the one of the peroneal nerve and the tibial nerve function is susceptible to the increase in expression of the one of IL-5, IL-6, IL-10, IL-12b, IL-21 and NGF genes in the neuronal cell in the treated foot.

2. The method of claim 1, wherein administering the PEMF treatment does not modulate expression of one of IL-la and IL-1B in the neuronal cell in the treated foot.

3. The method of claim 1, wherein the method comprises modulating one of an A-fiber and a C-fiber function associated with the one of the peroneal nerve and the tibial nerve function.

4. The method of claim 1, wherein the patient has a condition of painful peripheral diabetic neuropathy (PPDN).

5. A method of treating painful peripheral diabetic neuropathy (PPDN) in a patient in need thereof comprising:
   administering a plurality of PEMF treatments to the patient over a treatment period, each of the plurality of PEMF treatment comprising applying the PEMF treatment to a treated foot of the patient with a pulse frequency of about 1000 Hz and a pulse width of about 42 µs;
   promoting an increased nerve density in the treated foot over the treatment period by administering the PEMF treatment;
   modulating nerve function in the treated foot over the treatment period by administering the PEMF treatment; and
   producing a decrease in a pain score reported by the patient over the treatment period, by administering the PEMF treatment.

6. The method of claim 5, wherein modulation of nerve function comprises producing one of an increase in sympathetic skin response (SSR) waveform amplitude, a decrease in SSR time-to-onset, and an increase in nerve conduction velocity in the treated foot.

7. A method of modulating wound healing in a cell of a treated tissue of a patient in need thereof comprising:
   applying a PEMF treatment to the treated tissue of the patient, the PEMF treatment comprising a pulse frequency of about 1000 Hz and a pulse width of about 42 µs; and
   modulating expression of one of an HO-1, COX-2, ALOX-12, ALOX-15, PTGDS, PTGES, PTGIS, NOX, CAT, GSR, PRDX-6, and SOD-3 gene in the cell of the treated tissue; and measuring a first wound volume at a first time and a second wound volume at a second time;

wherein the cell is one of a dermal fibroblast cell, an epidermal keratinocyte cell, and a human monocyte cell;

wherein expression of one of the HO-1, COX-2, ALOX-12, ALOX-15, PTGDS, PTGES, PTGIS, NOX, CAT, GSR, PRDX-6, and SOD-3 genes in the cell of the treated tissue is susceptible to the PEMF treatment; and wherein the PEMF treatment produces a decrease in a wound volume between the first wound volume and the second wound volume.

8. The method of claim 7, further comprising modulating expression for PENK, PDYN, and POMC genes of an IMR-32 cell.

9. The method of claim 7, further comprising modulating one of the peroneal nerve and the tibial nerve function in the patient by applying the PEMF treatment to a foot of the patient.

10. The method of claim 9, wherein modulating the one of the peroneal nerve and the tibial nerve function comprises producing one of an increase in sympathetic skin response (SSR) waveform amplitude, a decrease in SSR time-to-onset, and an increase in nerve conduction velocity in the treated foot.

11. The method of claim 7, wherein the PEMF treatment is applied to a foot of the patient and comprises promoting an increased nerve density in the treated foot.

12. The method of claim 1, further comprising promoting an increased nerve density in the treated foot over a treatment period by administering the PEMF treatment.

13. The method of claim 1, further comprising modulating expression of one of an HO-1, COX-2, ALOX-12, ALOX-15, PTGDS, PTGES, PTGIS, NOX, CAT, GSR, PRDX-6, and SOD-3 gene in a cell of the treated foot.

14. The method of claim 1, further comprising measuring a first wound volume at a first time and a second wound volume at a second time.

15. The method of claim 1, further comprising promoting an increased nerve density in the treated foot.

16. The method of claim 1, further comprising producing a decrease in a pain score reported by the patient over a treatment period by administering the PEMF treatment.

17. The method of claim 5, further comprising modulating expression of one of an HO-1, COX-2, ALOX-12, ALOX-15, PTGDS, PTGES, PTGIS, NOX, CAT, GSR, PRDX-6, and SOD-3 gene in a cell of the treated foot.

18. The method of claim 5, further comprising modulating one of the peroneal nerve and the tibial nerve function in the patient by applying the PEMF treatment to a foot of the patient.

19. The method of claim 18, wherein modulating the one of the peroneal nerve and the tibial nerve function comprises producing one of an increase in sympathetic skin response (SSR) waveform amplitude, a decrease in SSR time-to-onset, and an increase in nerve conduction velocity in the treated foot.

* * * * *